(12) United States Patent
Senna et al.

(10) Patent No.: US 6,592,989 B1
(45) Date of Patent: Jul. 15, 2003

(54) METHOD FOR SYNTHESIS OF HYDROXYAPATITE, AND HYDROXYAPATITE COMPLEX AND METHOD FOR PREPARING THE SAME

(75) Inventors: Mamoru Senna, Chofu (JP); Tetsuhiko Isobe, Yokohama (JP); Manabu Kanayama, Kamakura (JP)

(73) Assignee: Nara Machinery Co., Ltd., Tokyo (JP)

( * ) Notice: Subject to any disclaimer, the term of this patent is extended or adjusted under 35 U.S.C. 154(b) by 0 days.

(21) Appl. No.: 09/701,181
(22) PCT Filed: Mar. 26, 1999
(86) PCT No.: PCT/JP99/01544
§ 371 (c)(1), (2), (4) Date: Nov. 27, 2000
(87) PCT Pub. No.: WO00/58209
PCT Pub. Date: Oct. 5, 2000
(51) Int. Cl.⁷ .................................................. B32B 5/16
(52) U.S. Cl. ..................... 428/402; 428/403; 428/407; 427/376.1; 427/376.2; 241/15; 241/16
(58) Field of Search ................................ 428/402, 403, 428/407; 427/376.1, 376.2; 241/15, 26

(56) References Cited

FOREIGN PATENT DOCUMENTS

| JP | 59-21509 | | 2/1984 |
|---|---|---|---|
| JP | 63-159207 | * | 2/1988 |
| JP | 63-159207 | | 7/1988 |
| JP | 5-32524 | * | 2/1993 |
| JP | 6-293505 | | 10/1994 |
| JP | 8-117323 | | 5/1996 |
| JP | 8-117323 A | * | 5/1996 |
| JP | 10-101823 | | 4/1998 |

* cited by examiner

Primary Examiner—Leszek Kiliman
(74) Attorney, Agent, or Firm—Oblon, Spivak, McClelland, Maier & Neustadt, P.C.

(57) ABSTRACT

The present invention provides a method of synthesizing hydroxy apatite comprising the steps of preparing a mixed material slurry by dispersing calcium hydroxide ($Ca(OH)_2$) powder into a phosphoric acid ($H_3PO_4$) solution; conducting a mechanochemical milling treatment in which shearing force and compressive force based on a centrifugal force of a mechanical rotating body are imparted to the mixed material slurry, and reacting the calcium hydrate component with the phosphoric acid component under normal temperature and pressure thereby to prepare hydroxy apatite (HAp) powder having fine crystals. According to the structure described above, there can be provided a method of synthesizing hydroxy apatite having fine and uniform particle size which can be directly synthesized under normal temperature and pressure in a short time through simple and single process.

24 Claims, 14 Drawing Sheets

METHOD FOR SYNTHESIS OF HYDROXYAPATITE, AND HYDROXYAPATITE COMPLEX AND METHOD FOR PREPARING THE SAME

TECHNICAL FIELD

The present invention relates to a method of synthesizing hydroxy apatite, hydroxy apatite composite and method of manufacturing the composite, more particularly relates to a synthesizing method, hydroxy apatite composite and method of manufacturing the same that are capable of manufacturing the hydroxy apatite and composite thereof having a high uniformity, fineness and an excellent dispersing property and capable of producing the hydroxy apatite and composite in a short time through a simple process.

BACKGROUND ART

A composition and structure of hydroxy apatite ($Ca_{10}(PO_4)_6(OH)_2$, hereinafter referred to simply as "HAp") are extremely similar to those of bone and tooth as biological inorganic components for constituting an organism body, so that HAp has a high affinity to the organism body. Therefore, HAp has been used as biomaterials, for example, as artificial organ material and medical material for constituting bone and tooth or the like. Further, HAp has been expected to be widely applied to various applications such as a material for absorbing/separating protein, amino acid, saccharides, DNA or the like; catalyst; inorganic ion-exchanger; and antibacterial agent or the like.

Conventionally, above described HAp has been manufactured in accordance with the following methods such as dry-method, wet-method and hydrothermal method. That is, as indicated by a combination of β-TCP with calcium carbonate or by a combination of calcium pyrophosphate with calcium carbonate, the dry method is a method of synthesizing the HAp, and the method comprises the steps of mixing calcium source and phosphoric acid source as starting materials to prepare a mixture; heating the mixture to a high temperature; and causing dry-type solid phase reaction thereby to synthesize HAp.

Further, for example, as indicated by a combination of calcium hydroxide suspended solution with phosphoric acid solution, the wet method is a method of synthesizing the HAp, and the method comprises the steps of mixing and reacting calcium source with phosphoric acid source as starting materials in a liquid phase to prepare a reaction product; and aging the reaction product at a high temperature thereby to synthesize HAp.

Furthermore, the hydrothermal method is a method of synthesizing the HAp, and the method comprises the steps of pressurizing a raw material of $CaHPO_4$ or the like in an autoclave to a pressure of several hundred atms; and heating the material to a temperature of 200° C. or more, thereby to synthesize HAp of single crystalline having a large grain size.

Thus synthesized HAp is excellent in affinity to organism body, so that applications of HAp as organism material have been tried and advanced in these years. However, the HAp synthesized by treating the raw material at a high temperature has a remarkably higher mechanical strength than that of organism bone. Therefore, when the HAp is assembled into the organism body as an alternate bone, there is raised a problem such that the HAp may damage or break an organism bone locating at circumference of the HAp. In addition, since the HAp as an inorganic compound has a small plastic deformability, it is difficult to utilize the HAp as the alternate bone.

To cope with this situation, there has been developed a HAp composite formed by compositing HAp with organic compounds such as collagen or the like that are capable of imparting the plastic deformability to the composite. As a method of manufacturing the composite of HAp and the organic compound for the purpose of synthesizing above bone-alternating material, the following methods have been tried.

Namely, there are used: a method comprising the steps of preparing a suspended solution into which calcium hydroxide is dissolved, preparing a phosphoric acid solution into which collagen is dissolved, and dropping the phosphoric solution into the suspended solution; a method comprising the steps of previously synthesizing a HAp precursor, mixing the HAp precursor into a collagen suspended solution to form a mixture, and thereafter, freeze-drying (lyophilizing) the mixture; and a method in which a HAp-collagen composite is synthesized in a solution into which anionic or cationic polymer in place of the above collagen is dissolved.

As described above, as a method of synthesizing the HAp and a method of manufacturing the HAp composite composed of HAp and the organic compound, various methods have been adopted.

The above dry-method as a method of synthesizing HAp is more excellent than the wet-method in a point that HAp having a stoichiometric composition can be synthesized. In contrast, however, the dry-method may pose problems such that a pulverizing operation after completion of a heat treatment is required to be continued for a long period of time, so that there is a disadvantage in productivity, and crystals cannot be uniformly formed and stable characteristics cannot be obtained.

Further, according to the wet-method, it becomes possible to obtain a HAp powder having a relatively fine grain size and a large specific surface area. In contrast, however, in order to secure the stoichiometric composition, a strict pH control and temperature adjustment are required, thus making a operation control of the manufacturing apparatus complicate. Further, the wet-method poses problem such that a production efficiency is extremely lowered because the synthesizing reaction requires a long period of time and the aging process to be performed at the high temperature also requires a long period of time.

On the other hand, according to the hydrothermal method, there can be obtained HAp whiskers composed of plate crystals having a high crystallizing property or HAp whiskers, having an extremely large size, of which crystal axis is extended in a C-axis direction. In contrast, however, the hydrothermal method requires a high-pressure and heat resisting apparatus as a synthesizing apparatus, so that an apparatus initial cost would be remarkably increased and the method requires long period of time for performing the synthesizing reaction, whereby there is posed a problem that the manufacturing efficiency is disadvantageously lowered.

The above problem is commonly revealed in any of the methods of manufacturing the HAp composite composed of HAp and organic compound. In any of the methods, there is posed problems such that manufacturing process and operation control of the apparatus are complicated, a long term manufacturing time is required and the resultant HAp product is formed to be coarse and non-uniform.

The present invention had been achieved to solve the aforementioned problems and an object of the present invention is to provide a method of synthesizing HAp, the method being capable of directly synthesizing HAp crystalline powder having fine and uniform size by a single process in a short time under a normal temperature and normal pressure without treating material at high temperature and high pressure and without forming a precursor as formed in the conventional methods.

Further, another object of the present invention is to provide HAp composite which can be used as a bone-alternating material by utilizing the aforementioned synthesizing method, and to provide a manufacturing method which can synthesize the composite through a simple and single process.

DISCLOSURE OF THE INVENTION

In order to achieve the aforementioned objects, the inventors of the present invention had prepared HAp powders under various conditions by using various material powders, reacting synthesizing method and pulverizing devices (grinding machines). Then, through the many experiments, the inventors had comparatively reviewed the influences of the differences in the manufacturing conditions onto characteristics and manufacturing cost of the HAp powder and the HAp composite.

As a result, the inventors had found and obtained the following knowledge. That is, when calcium hydroxide powder as a raw material and organic compound particles as required are mixed into phosphoric acid solution thereby to prepare a mixed material slurry then the slurry is subjected to a mechanochemical milling treatment in which shearing force and compressive force based on the centrifugal force of a mechanically-rotating body are imparted to the mixed material slurry thereby to perform the mixing and milling operation, a hydroxy apatite powder and a composite thereof having a fine particle size and uniform characteristics can be effectively manufactured in a short time under normal temperature and pressure.

In particular, when a multi-ring media type ultrafine mill comprising a number of ring-shaped pulverizing media is used as a mixing and milling device for advancing a mechanochemical reaction by conducting the mixing and milling of the mixed material slurry, there could be also obtained the findings such that a reaction activity of the mixed material slurry was increased, it became possible to rapidly advance the above mechanochemical reaction whereby a production efficiency of the HAp powder and the composite thereof could be remarkably increased.

Furthermore, in the conventional various synthesizing methods, a solid component content (concentration) and viscosity of the mixed material slurry was required to be suppressed to a lower level, and the mixed material slurry was required to be mixed and pulverized for a long time. However, when the above ultrafine mill is used, even if the slurry has a high solid content and a high viscosity, it became possible to mix and pulverize the slurry in a short time whereby the production efficiency of the HAp powder and the composite thereof could be remarkably increased.

The present invention has been achieved on the basis of the above findings. Namely, a method of synthesizing HAp comprises the steps of preparing a mixed material slurry by dispersing calcium hydroxide ($Ca(OH)_2$) powder into a phosphoric acid ($H_3PO_4$) solution, conducting a mechanochemical milling treatment in which shearing force and compressive force based on a centrifugal force of a mechanical rotating body are imparted to the mixed material slurry, and reacting the calcium hydroxide component with the phosphoric acid component under normal temperature and pressure thereby to prepare HAp powder composed of fine crystal grains.

Further, in the above synthesizing method, a centrifugal effect Z to be imparted to the slurry by a centrifugal force caused in the mechanochemical milling treatment is preferable to be 15 or more. In this connection, the centrifugal effect Z is a quantitative index showing a magnitude of pulverizing force, and is defined as a ratio of the centrifugal force Fc to a gravitational force Fg. The centrifugal effect Z is expressed by the following formula:

$Z = Fc/Fg = r\omega^2/g$ (-)

wherein r is radius of rotation, $\omega$ is angular speed, and g is gravitational acceleration.

Further, Ca/P molar ratio of the mixed material slurry is preferably set to a range of 1.2–1.8. In addition, a solid content of the mixed material slurry is preferably set to a range of 5–40 wt %.

In addition, a HAp composite according to the present invention comprises HAp particles formed by reacting calcium hydroxide ($Ca(OH)_2$) with phosphoric acid ($H_3PO_4$) under a condition of existing organic compound particles and the organic compound particles of which surfaces are integrally formed and composited with the HAp particles.

Further, in the above HAp composite, Ca/P molar ratio is preferably set to a range of 1.2–1.8. In addition, the organic compound is preferably formed of fiber protein composed of at least one of silk fibroin (SF) and collagen. Further, a ratio of the fiber protein to the composite is preferably set to 10–90 wt %. Since a ratio of the fiber protein contained in organism bone is about 20%, when the composition of the composite is intended to be close to that of organism structure, it is more preferable that the ratio is set to a range of 10–40 wt %.

Further, a method of manufacturing a HAp composite according to the present invention comprises the steps of preparing a mixed material slurry by dispersing calcium hydroxide ($Ca(OH)_2$) powder and organic compound particles into a phosphoric acid ($H_3PO_4$) solution, conducting a mechanochemical milling treatment in which shearing force and compressive force based on a centrifugal force of a mechanical rotating body are imparted to the mixed material slurry, and reacting the calcium hydroxide component with the phosphoric acid component under normal temperature and pressure whereby HAp powder having fine crystals is deposited onto surfaces of the organic compound particles, simultaneously HAp powder and the organic compound are composited.

In the above manufacturing method, it is preferable that the organic compound particles are subjected to the mechanochemical milling treatment in advance in a phosphoric acid solution so that phosphoric acid ion having affinity is adhered to the surface of the organic compound particles. Further, a centrifugal effect Z to be imparted to the slurry by a centrifugal force caused in the mechanochemical milling treatment is preferably set to 15 or more. Further, Ca/P molar ratio of the mixed material slurry is preferably set to a range of 1.2–1.8. In addition, a solid content of the mixed material slurry is preferably set to a range of 5–40 wt %.

Further, the organic compound is preferably formed of fiber protein composed of at least one of silk fibroin (hereinafter referred to simply as "SF") and collagen. Further, a ratio of the fiber protein to the composite is preferably set to 10–90 wt %. The ratio is more preferably set to a range of 10–40 wt %. In particular, it is preferable that the mechanochemical milling treatment for the mixed material slurry is performed by means of a multi-ring type ultrafine mill comprising a number of ring-shaped pulverizing media.

The present invention adopts a countermeasure such that a mixed material slurry is prepared by mixing calcium hydroxide $(Ca(OH)_2)$ as calcium source into a phosphoric acid $(H_3PO_4)$ solution as phosphoric acid source, then conduct a mechanochemical milling treatment in which shearing force and compressive force based on a centrifugal force of a mechanical rotating body are imparted to the mixed material slurry, and cause a mechanochemical reaction i.e. a mutual reaction between acid-base points at surfaces of the material particles whereby HAp powder having fine crystals is synthesized in a short time under normal temperature and pressure.

More concretely to say, the method of synthesizing HAp powder comprises the simple steps of preparing the mixed material slurry by weighing and mixed phosphoric acid solution and calcium hydroxide so as to establish a molar ratio (Ca/P) of calcium and phosphor to be 1.2–1.8, and putting the slurry into a vessel of a pulverizing apparatus and mixing and milling the slurry under a predetermined pulverizing condition.

In addition, when organic compound particles are previously added to the mixed material slurry in advance and the slurry is subjected to the same mixing and milling treatment, there can be effectively manufactured HAp composite in which HAp particles are integrally formed to the surface of the organic compound particles.

As the organic compound particle described above, there can be used particles composed of fiber proteins such as SF and collagen or the like which have a high affinity with respect to organism body. These fiber proteins have a function of imparting a plastic deformability to the HAp composite. In a case where an organism material is formed by using this composite, there is no fear that the material would damage or break the organism structure located around the material, and the affinity to the organism body can be remarkably increased.

It is preferable that a ratio of the fiber protein to the composite is set to a range of 10–90 wt %. When this ratio is less than 10 wt %, the plastic deformability of the composite is insufficient. On the other hand, when the ratio is greater than 90 wt %, the ratio of HAp as an organism-applicable substance is relatively lowered, so that the composite becomes unsuitable for the organism material. In particular, in order to make the composite more close to the composition of the organism structure, the ratio of protein is more preferably set to a range of 10–40 wt %.

In addition, when the organic compound particles are previously subjected to the mechanochemical milling treatment in the phosphoric acid solution, phosphoric acid ions can be adhered to the surface of the organic compound particles so as to exhibit an affinity. As a result, a nucleation (nucleus formation) of the calcium phosphate salts including HAp is induced by calcium ions dissolved in a liquid phase, and the nucleation is induced at the surface of the organic compound particles of SF or the like composed of hydrophobic amino acids such as glycine and alanine or the like. In addition, since a particle size of the organic compound per se is lowered, there can be also provided another effect of increasing nucleation site. Therefore, the synthesizing reaction of HAp at the surface of the organic compound particles can be promoted. Further, a bonding strength between an organic compound particle and a HAp particle is increased, whereby HAp composite having stable characteristics can be obtained.

Further, when Ca/P molar ratio of the mixed material slurry or HAp composite is set to a range of 1.2–1.8, HAp having a predetermined stoichiometric composition can be formed and there can be obtained HAp powder and composite thereof having less contents of by-product and impurities.

In addition, when a part of calcium hydroxide $(Ca(OH)_2)$ is replaced by calcium carbonate $(CaCO_3)$, $CO_3^{2-}$ group can be introduced into a part of $OH^-$ group in hydroxy apatite (HAp). When the above $CO_3^{2-}$ group is introduced, it become possible to form HAp material having properties similar to those of organism structure.

In the synthesizing method and manufacturing method of the present invention, a solid content of the mixed material slurry is set to a range of 5–40 wt %.

When the above solid content is less than 5 wt %, even if the milling treatment capable of imparting high impact to the slurry is conducted, the reaction cannot be quickly advanced thereby to lower the production efficiency of HAp. Namely, if the content of solid component as reacting component is not so high to some degree, the imparted impact energy is liable to be wasted thereby to lower the energy efficiency. On the other hand, when the solid content exceedingly increased to 40 wt % or more, an uniform milling treatment becomes difficult and the product characteristics become also non-uniform. Therefore, the solid content is set to a range of 5–40 wt %, however, a range of 10–35 wt % is more preferable.

According to the synthesizing method and the manufacturing method of the present invention, the mechanochemical reaction is advanced in a process where the mixed material slurry is subjected to the milling treatment, thereby to form HAp powder and composite thereof.

As the milling device or attritor for promoting the mechanochemical reaction by mixing and milling the above mixed material slurry, a motor-driven mortar and various types of ball mills are considered to be adopted. However, in these milling devices, a centrifugal effect is relatively small, and mechanical stress and impacting force to be imparted to the material are insufficient. Therefore, even if the milling operation is carried out for about one hour or so, it is very difficult to impart sufficient reactivity to the mixed material and also difficult to advance the mechanochemical reaction. For this reason, in general, the reaction activity cannot be imparted to the mixed material slurry until the material slurry is subjected to the treatment for a long time of about 10–50 hours or more. Accordingly, the above milling devices are not considered to be effective for simplifying the manufacturing processes.

Therefore, in the synthesizing method and manufacturing method of the present invention, it is preferable to adopt various impacting-type grinding mills or a powder surface modifying device capable of repeatedly imparting an impacting force to the mixed material in a short time.

In the mixing and milling treatment for advancing the above mechanochemical reaction, the centrifugal effect Z to be imparted to the mixed material slurry is required to be at least 15. When the centrifugal effect Z is less than 15, the impacting force to be imparted to the mixed material slurry is insufficient, and it becomes impossible to increase the reaction activity for forming distortions in crystal structure of the surface portion of the material particles in a short time. Therefore, in order to increase the reaction activity of the mixed material slurry and to prepare the mixed material slurry having an uniformity, it is required to use a milling device capable of imparting impacting force having a centrifugal effect Z of 15 or more, preferably 70 or more, and more preferably 150 or more.

In this connection, the method of the present invention therefore uses such an ultrafine mill (micronizer:multi-ring type pulverizing mill) as shown in FIGS. 1 and 2 as the grinding device comprising a number of ring-shaped pulverizing media for rapidly carrying out the mechanochemical treatment. This ultrafine mill is capable of applying impact force and friction to powder particles so as to enhance the reactivity thereof, and efficiently mixing and milling the powder particles within a short time. The device comprises a cylindrical casing 1, a main shaft 4 which is rotated in the casing 1, and a plurality of sub-shafts 6 which are rotated around the main shaft 4 in linage with the rotation of the main shaft 4, wherein each of the sub-shafts 6 being provided with many ring members 9 as grinding media. Although the size of each of the ring members 9 as the grinding media depends upon the type and size of the treatment device used, the outer diameter of the ring member 9 is 25 to 45 mm, and the thickness thereof is several mm. Although the material for constituting the ring members 9 depends upon the physical properties of a material to be processed, the ring members 9 can be composed of stainless steel, ceramic materials such as alumina, zirconia or the like, or a hard carbide material such as WC.

The casing 1 has an internal peripheral surface 2 having a longitudinal axis, and a rotational mechanism 3 provided in the casing 1 serving as a processing chamber. The rotational mechanism 3 comprises the main shaft 4 concentric with the casing 1, a pair of press plates 5 and 5' which are fixed at a predetermined interval therebetween in the longitudinal direction of the main shaft 4, and the sub-shafts 6 which are fixed by the press plates 5 and 5' so as to be arranged at the same distance from the main shaft 4 in parallel therewith.

Each of the press plates 5 and 5' has a form in which the same number of arms as the number of the sub-shafts 6 are radially projected. The form of the press plates 5 and 5' in which the arms are provided at equal intervals, not a simple disk form, can improve the degree of convection (mixing) of a material to be processed, which is put into the casing 1, and decrease as much as possible the amount of the material to be processed, which is deposited as a dead stock on the upper press plate 5.

Each of the sub-shafts 6 comprises a long bolt-like member having ends that are respectively passed through holes provided at the ends of the arms of both press plates 5 and 5' and tightened by nuts 7. The upper end of the main shaft 4 is connected directly to a driving source such as a motor (not shown) or provided with a pulley so that the rotational force of the driving source is transmitted to the main shaft 4 through a V belt.

As shown in FIG. 2, a cylindrical collar 8 is fitted on each of the sub-shafts 6 with a small gap therebetween, and a plurality of ring members 9 are retractably mounted on each of the collar 8. Each of the ring members 9 has an internal diameter sufficiently larger than the outer diameter of the collar 8, and is constructed so as to have a sufficient gap between the internal peripheral surface of the ring member 9 and the external peripheral surface of the collar 8 when the external peripheral surface of the ring member 9 contacts the internal peripheral surface 2 of the casing 1.

The ring members 9 are stacked to form a gap corresponding to the total thickness of 2 to 3 ring members 9 between the upper side of the uppermost ring member 9 and the lower side of the press plate 5, but not closely stacked between both press plates 5 and 5' without a gap. This stacking structure makes the ring members 9 rotatively around each of the collars 8.

Each of the ring members 9 is formed in a cylindrical form having parallel upper and lower surfaces, which is a so-called washer-like form having smooth upper and lower surfaces, and an outer peripheral surface. If required, the outer peripheral surface may be curved for promoting bite into the powder material.

Agitating blades 10 and 10' are radially disposed at upper and lower portions of the main shaft 4, which are below the lower press plate 5' and above the upper press plate 5, respectively, so as to agitate the material to be processed, which is put into the casing 1.

To an upper flange 13 of the casing 1 is fixed an upper cover 11 having a through hole by tightening members such as bolts and nuts, with a packing 12 therebetween. The main shaft 4 is passed through the through hole of the upper cover 11, the through hole being provided with an oil seal 14 for sealing the main shaft 4, and an oil seal holder 15 for holding the oil seal 14. In order to prevent a temperature rise of the material to be processed during grinding, the side of the casing 1 has a jacket structure 16. A refrigerant supply port 17 and discharge port 18 are provided in the jacket 16 so that the material to be processed which is put into the casing 1 can be cooled by continuously supplying any one of various refrigerants into the jacket 16.

In the grinding device (micronizer) constructed as described above, a gap of several mm is formed between the outer periphery of each of the sub-shafts 6 and the inner peripheries of the ring members 9 so that the ring members 9 can be freely independently rotated. The ring members 9 serving as the grinding media are radially moved by an amount corresponding to the gap due to the centrifugal force generated by the rotation of the main shaft 4, and circumferentially rotated in the casing 1 while being pressed on the inner periphery 2 of the casing 1. At the same time, the ring members 9 themselves are rotated around the sub-shafts 6 due to the friction between the inner peripheral surface 2 and the ring members 9. Namely, the ring members 9 are moved in the casing 1 while being repeatedly rotated around the main shaft 4 and each of the sub-shafts 6.

When the raw material mixture powder in an amount corresponding to 10 to 80% of the effective volume of the grinding portion is put into the casing 1 and then subjected to the mechanochemical treatment by rotating the main shaft 4, the raw material mixture powder is held between the rotating ring members 9 and the internal peripheral surface 2 of the casing 1, and subjected to impact force (compressive/shear force) corresponding to the centrifugal effect caused by the ring members 9 and the grinding function due to the rotation of the ring members 9 themselves. As a result, the raw material mixture powder is ground and dispersed, and, at the same time, strains and distortions are produced in the crystal structure of the particle surfaces of the mixture powder to form a precursor in which the reactivity of the surfaces of the raw material mixture powder is enhanced. The centrifugal effect Z exerted on the raw material mixture powder is controlled by changing the rotational speed of the main shaft 4.

According to knowledge of the inventors of this invention, it has been confirmed that the mechanochemical reaction to be advanced by mixing and pulverizing the mixed material slurry is greatly influenced by operating conditions such as a kind or magnitude of the mechanical stress, pulverizing mechanism of the milling device, atmosphere for the treatment, or the like.

In place of the conventional milling devices such as motor-driven mortar, various ball mills or the like, when there is particularly used a milling device like the above multi-ring media type ultrafine mill having a special pulverizing mechanism provided with a number of ring-shaped pulverizing media, the reactivity of the material mixture can be rapidly increased by the short-time mixing and pulverizing treatment, so that it becomes possible to shorten a required time for the mechanochemical reaction.

The above reaction mechanism to be used in the method of this invention is quite different from that of the conventional mechanochemical reaction mainly consisting of a liquid phase reaction disclosed in Japanese Patent Publication No. 3 (1991)-69844 in which a dissolving of solid material is promoted by a wet-type pulverization then a compositing reaction is advanced by a mutual reaction of ions generated in a solution thereby to cause the liquid phase reaction.

That is, the method of this invention is a method wherein acid-base points are generated at the surface of the solid material particles by utilizing the mechanical stress i.e., mechanical energy caused by the mechanical rotating body, and simultaneously cause the mutual reaction. In this point, the reaction mechanism in this invention is also quite different from that of the conventional solid-phase method i.e., a high temperature solid-phase reacting method in which a interaction mutual reaction between different material particles is advanced by using thermal energy thereby to form HAp.

In particular, non-free water such as hydroxyl group and bound water (crystal water) is quite different from free water to be added to the material powder as dispersion medium in the conventional method. The non-free water directly contributes to form a bridge-bonding for advancing the mechanochemical compositing reaction to be caused during the mixing and milling the material mixture. Accordingly, when the calcium hydroxide powder having the non-free water i.e., hydroxyl group is used as a starting material like this invention, the mechanochemical reaction can be rapidly advanced in the mixing/milling process thereby to effectively produce HAp.

When the slurry containing Hap powder obtained by conducting the above mechanochemical milling treatment is dehydrated and dried at normal temperature, there can be obtained fine and spherical HAp crystal powder or composite thereof having a primary grain size of about 50 nm.

In addition, when the above dehydrated and dried HAp or the composite thereof is compressed by a uniaxial compression method, a biaxial compression method, or a cold isostatic pressing (CIP) method, there can be formed a densified organism bone alternating material having an arbitrary-shape.

Furthermore, since the HAp slurry obtained by being subjected to the mechanochemical milling treatment can be provided as fine crystal slurry with a good dispersibility, when this slurry is molded by a casting method, there can be formed a densified organism material having an arbitrary-shape.

The mechanochemical reaction does not easily take place. However, in the present invention, the mechanochemical reaction is promoted by using a milling device capable of imparting a particularly strong mechanical impact function. According to the above method, there can be manufactured a fine HAp powder and a composite thereof having a uniform chemical composition and a grain size without requiring a complicated pH adjustment essentially required for the conventional wet-method or without using a long-time pulverizing treatment or the like which had been an essential treatment in the conventional dry-method.

According to the method of the present invention, there can be obtained a fine HAp powder and a composite thereof having a relatively uniform grain size under normal pressure and temperature in a short time in comparison with the conventional method. Therefore, when the above HAp or the like is composited with various organic materials having a less durability at high-temperature, a possibility of capable of forming various organism materials can be increased.

For example, when a HAp film is integrally formed onto a surface of an organic substrate having flexibility, there can be formed an organism material having a plastic deformability (flexibility). More concretely to say, when the organic substrates such as composed of nylon, cuttlefish skin, chitosan or the like is dipped into a HAp slurry for about 30 seconds, the slurry being obtained by conducting the mechanochemical milling treatment previously described above, thereafter, the dipped substrate is pulled up from the slurry at a pulling speed of about 1 mm/sec., then the slurry adhered to the substrate is dried at a temperature of about 50° C., so that there can be obtained an organism material (HAp composite) in which a dense HAp layer is integrally formed onto the surface of the organic substrate.

In addition, when the HAp film is integrally formed onto a surface of materials such as various metals, ceramics, or polymer materials or the like in place of the organic substrates described above, there can be also formed an organism material. The above HAp film is extremely dense and can be bonded to a body material with a high bonding strength, so that a crack-formation is hardly occurred. Accordingly, there can be provided the organism materials excellent in durability and reliability.

According to the method of synthesizing HAp, HAp composite and the method of manufacturing the composite of the present invention, the HAp powder is formed by conducting the mechanochemical milling treatment imparting shearing force and compressive force based on the centrifugal force of the mechanically rotating body, so that a fine crystal HAp powder having a uniform size or the composite thereof can be manufactured in a short time through a simple process even under the conditions of normal temperature and pressure.

Further, when the organic compound particles are contained in the mixed material slurry and HAp is synthesized under a condition of existing the organic compound, the HAp composite comprising HAp and the organic compound can be easily manufactured through a single process under the normal temperature and pressure.

In particular, the particle size of each of the HAp powder and the composite thereof is fine to be about 50 nm and a dispersing state of the particles is also good, so that a dense organism material having less crack-formation can be formed whereby it is possible to provide the organism material having high durability and reliability.

BEST MODE FOR EMBODYING THE INVENTION

Next, embodiments of the present invention will be explained on the basis of the following Examples and Comparative Examples.

EXAMPLE 1

Ion-exchanged water was added to 21.2 cm$^3$ of phosphoric acid ($H_3PO_4$) solution of a percentage content of 85% (mfd. by Daisei Kagaku K. K.) thereby to prepare a 200 cm$^3$ of diluted solution. Then, 36.96 g of calcium hydroxide ($Ca(OH)_2$) powder (mfd. by Wako Junyaku kogyo K. K.) was added to the diluted solution so that Ca/P molar ratio is controlled to be 1.67, thereby to prepare a mixed material slurry.

Figure 1:
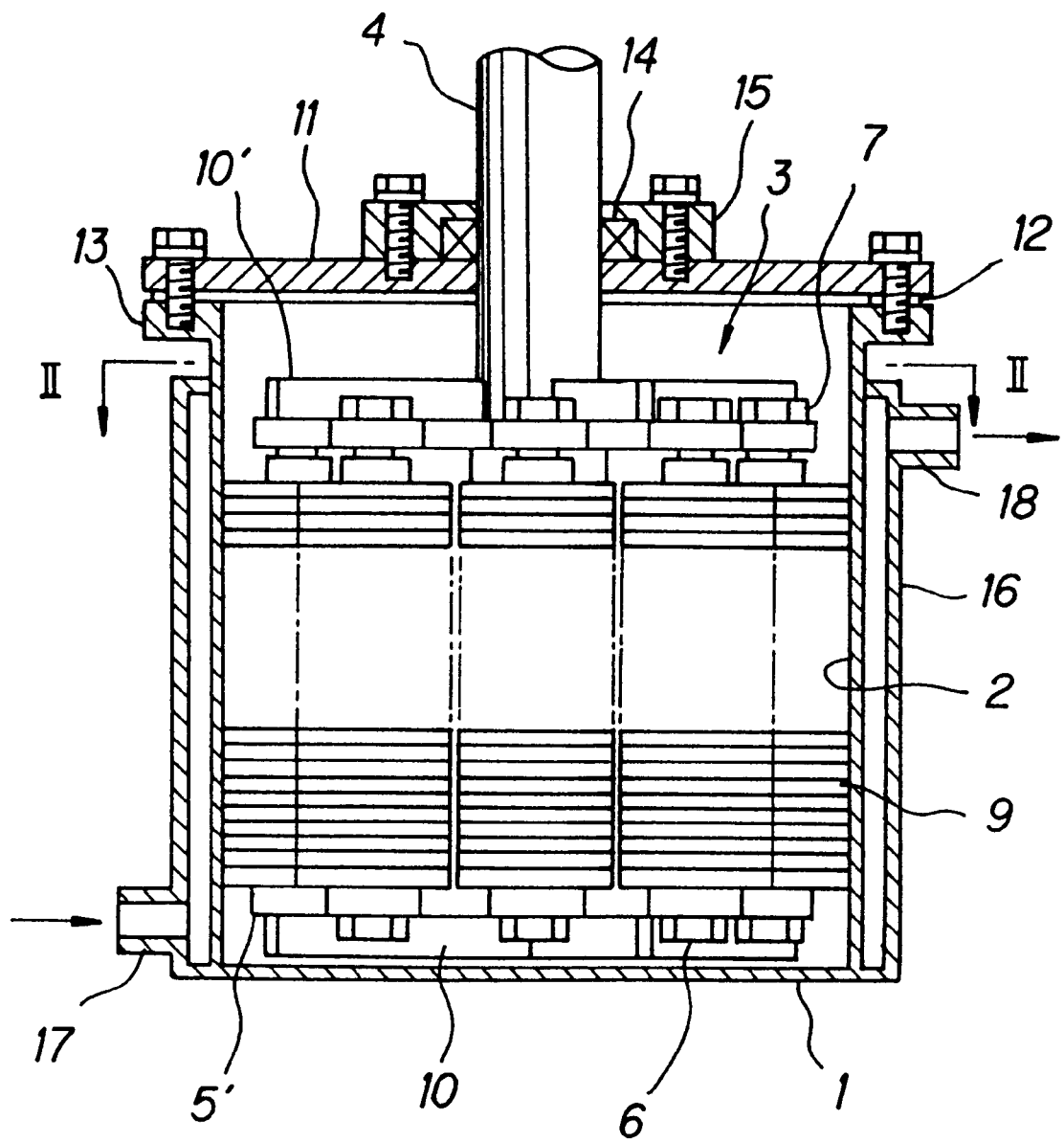
FIG. 1 is a cross sectional view showing a structure of a milling device used in the method of the present invention.
Figure 2:
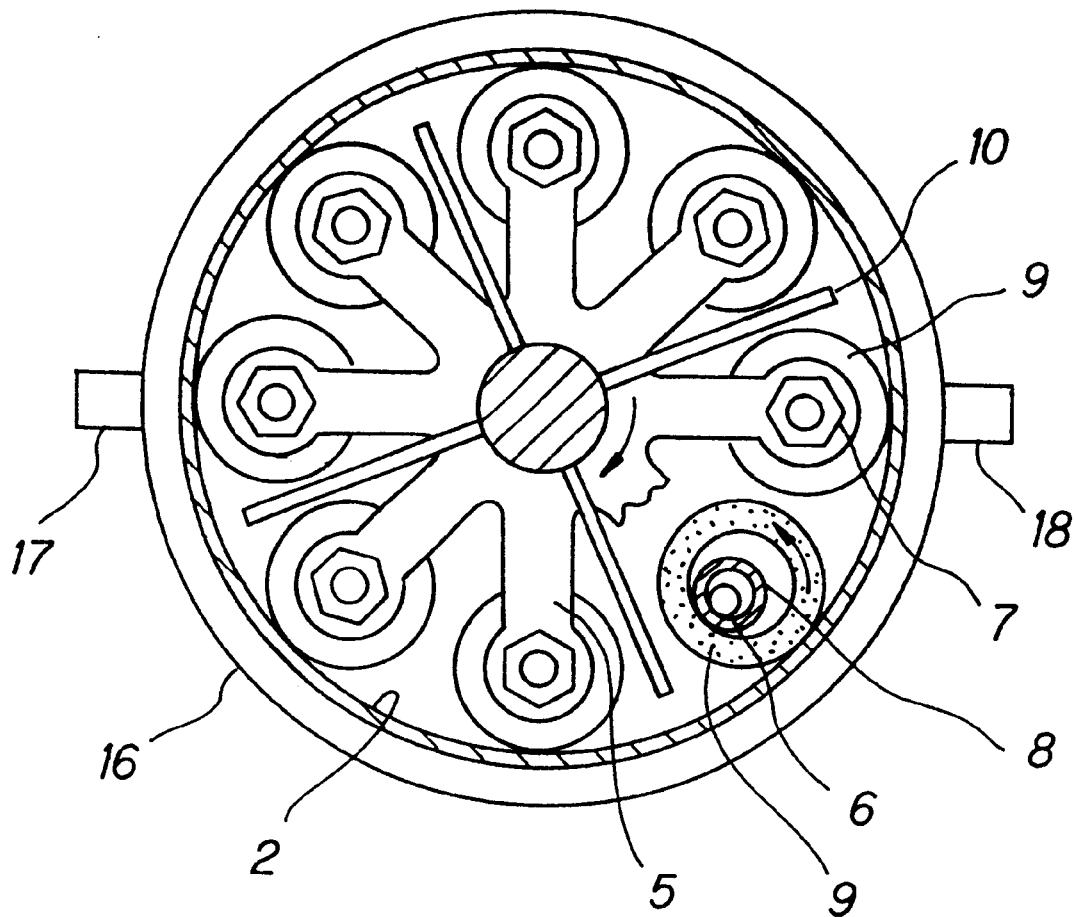
FIG. 2 is a cross sectional view taken along the line II—II of FIG. 1.

This mixed material slurry was put into a casing 1 of a multi-ring media type ultrafine mill (MICROS-O type mill. mfd. by K. K. Nara Kikai Seisakusho, technical specification: zirconia ring) shown in FIGS. 1 and 2. Under a state where a cooling water having a temperature of 15° C. was circulated in a jacket 16 provided to an outer peripheral portion of the casing 1 thereby to keep the temperature of the casing 1 to be a constant value, the rotation speed of the main shaft 4 was set to 850 rpm and the mechanochemical milling treatment for the mixed material slurry was carried out for 5 minutes, 15 minutes, 60 minutes and 180 minutes, respectively, so that each of the mixed material slurry was subjected to the mechanochemical treatment in which shearing force and compressive force based on the centrifugal force of the ring-shaped members 9 as the mechanical rotating body were imparted to the each of mixed material slurry. The centrifugal effect Z during the above mixing and grinding operation was 35.

Due to the above mechanochemical milling treatment, the phosphoric acid component and the calcium hydroxide component were reacted in accordance with the following reaction formula (1):

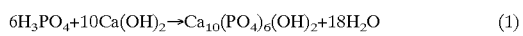

$$6H_3PO_4 + 10Ca(OH)_2 \rightarrow Ca_{10}(PO_4)_6(OH)_2 + 18H_2O \qquad (1)$$

thereby to obtain a slurry containing HAp.

Then, thus obtained each of the slurry was subjected to a suction filtration thereby to separate a formed product. Then, the formed product was dried for 24 hours in a thermostatic drying chamber of which temperature was controlled to be 50° C. thereby to prepare respective fine crystalline HAp powders of Example 1.

COMPARATIVE EXAMPLE 1

HAp powder of Comparative Example 1 was prepared by treating a the mixed material slurry was subjected to a stirring treatment for 12 hours by using a general purpose magnetic stirrer in place of the multi-ring medium type ultrafine mill (MICROS) used in Example 1.

With respect to the HAp powders of Example 1 and Comparative Example 1, particle shape, grain size and dispersing state of the HAp powders were observed by means of a scanning type electron microscope (SEM: mfd. by Nippon Denshi K. K. JEOL, JSM-30S) and a transmission type electron microscope (TEM: mfd. by Nippon Denshi K. K. JEM-2000FX11). As a result, each of the HAp powders of Example 1 was confirmed to be fine so as to have a grain size of about 30–50 nm and have an extremely comfortable dispersed state. It was confirmed that HAp crystal having an uniformity and fineness could be synthesized in a short time. It was also confirmed that the sample which had been subjected to the milling treatment for 180 minutes was entirely changed to spherical aggregated particles having a grain size of 0.5 μm and having no anisotropy.

On the other hand, in Comparative Example 1, in spite of that the stirring treatment was continued for a long time of 12 hours, the obtained HAp powder was confirmed to be consisted of coarse crystals having grain size exceeding 10 μm. A production yield of HAp was low as 60–70% thereby to be found that the synthesizing reaction could not be advanced quickly.

Further, a Ca/P molar ratio of each HAp powders was measured by means of a fluorescent X-ray analyzing device (XPF: mfd. by Rigaku Denki Kogyo K. K., 3080E2). As a result, a stoichiometric ratio of HAp sample obtained by conducting the milling treatment for 180 minutes was lower than 1.67 which was the Ca/P molar ratio in the material slurry, and it was confirmed that there was produced Ca-defective type HAp. The reason is considered that $Ca(OH)_2$ existing in an amorphous state is dissolved into the liquid phase whereby phosphoric acid ion remaining in the liquid phase forms a calcium salt, so that the phosphoric acid is changed to exist as a solid body.

Figure 3:
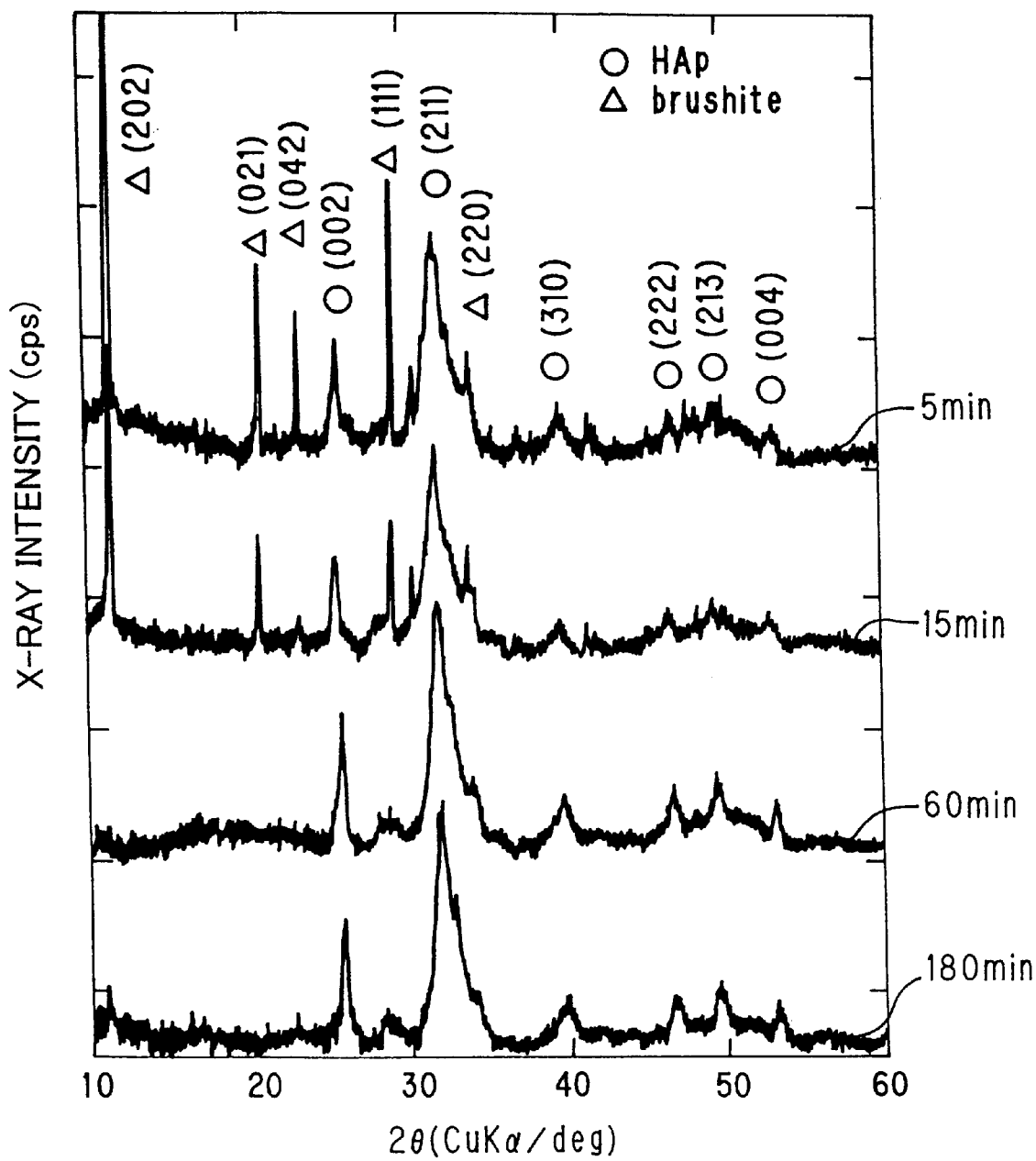
FIG. 3 is a graph showing an X-ray diffraction (XRD) profile of a HAp powder.

Furthermore, with respect to each of the HAp powders, analysis of crystalline structure was performed by using a powder X-ray diffraction device (XRD: mfd. by Rigaku Denki Kogyo K. K., Rint 2000). The results are shown in FIG. 3. That is, in the sample prepared by being subjected to the mechanochemical milling treatment for 5 minutes, there was intensively revealed a diffraction peak of brushite ($CaHPO_2 \cdot H_2O$; hereinafter referred to simply as "BS"). In addition, the diffraction peak intensity originated from the HAp was intensified and there were observed diffraction peaks at crystal surfaces other than (002) surface and (211) surface.

In addition, with respect to the sample prepared by the milling treatment for 15 minutes, a diffraction peak of BF was remained. With respect to the sample prepared by the treatment for 60 minutes, the diffraction peak of BF was completely eliminated so as to form a single phase of HAp. As described above, in accordance with the time of the milling treatment, the synthesizing reaction as shown in the following reaction formula (2) is advanced in a short time while forming BS as an intermediate product.

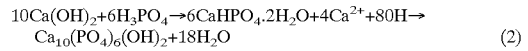

$$10Ca(OH)_2 + 6H_3PO_4 \rightarrow 6CaHPO_4 \cdot 2H_2O + 4Ca^{2+} + 8OH^- \rightarrow Ca_{10}(PO_4)_6(OH)_2 + 18H_2O \qquad (2)$$

The above crystalline structure of BS is similar to that of HAp and positions of Ca at (010) surface and (110) surface in BS are almost coincide with those of at the respective crystal surfaces in HAp. Therefore, such calcium is considered to be calcium phosphate which is produced as an intermediate product during a formation of bone in organism body.

In addition, a change in chemical states such as bonding state of each phosphoric acid ions ($HPO_4^{2-}$, $H_2PO_4^{3-}$) and hydroxyl group were measured by using an infrared absorption (FT-IR) spectrum measuring device (BIO-RAD, FTS-65, mfd. by Nippon Bio.Rad Laboratories K. K.). The measured results are shown in FIG. 4.

Figure 4:
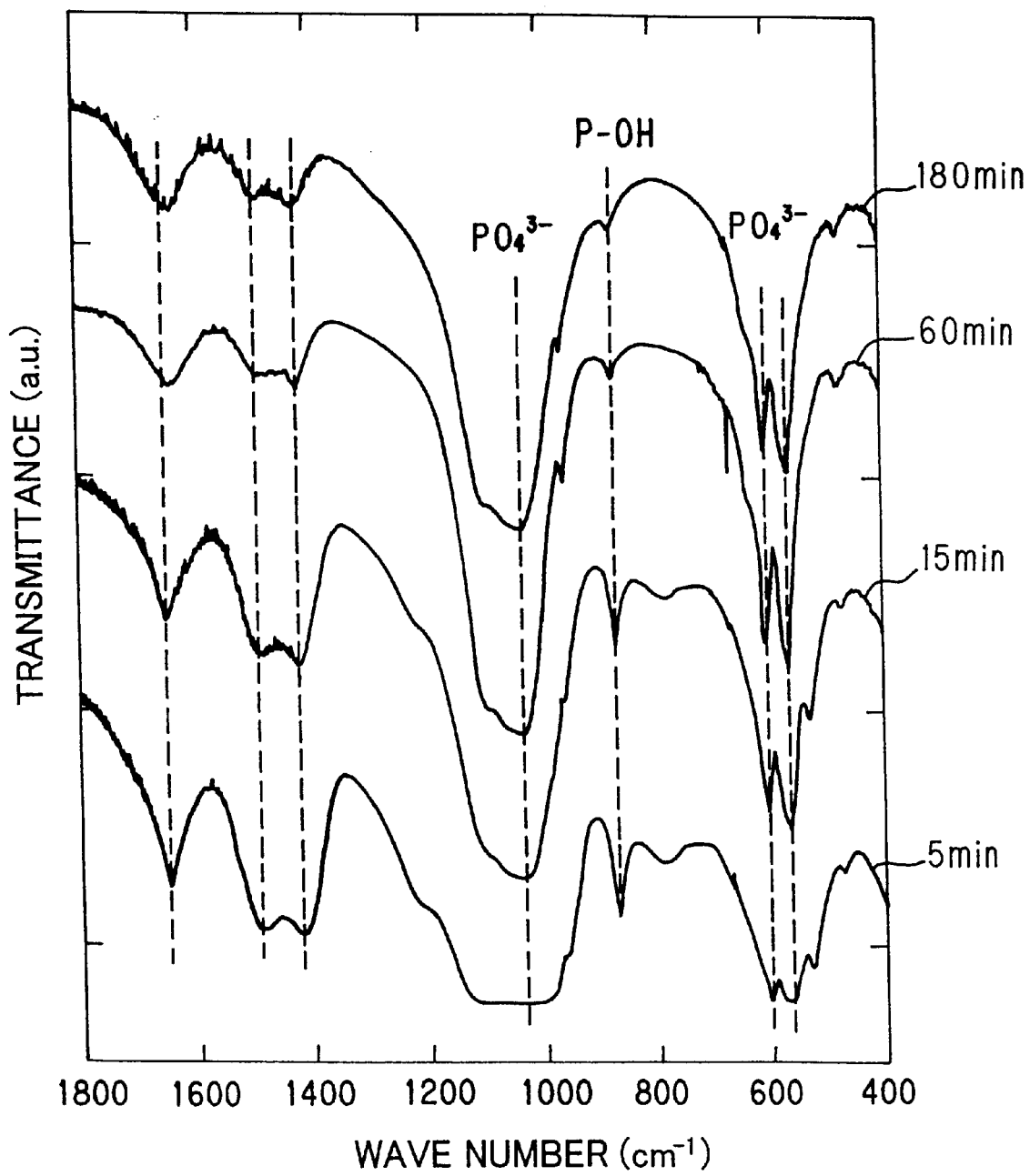
FIG. 4 is a graph showing an infrared absorption (FT-IR) spectrum of a HAp powder.

As is clear from the results shown in FIG. 4, an absorption peak intensity based on P-OH stretching vibration at a wave number close to 875 $cm^{-1}$ was gradually weakened as the milling time was increased. However, even if the milling treatment was conducted for 180 minutes, the absorption peak was slightly remained. This proved the following facts that BS had remained as an amorphous phase and that $HPO_4^{2-}$ ion existed in $PO_4^{3-}$ ion site of HAp thereby to form Ca-defective type apatite.

Each of the absorption peaks (565, 602, 965, 1034 $cm^{-1}$) originated from $PO_3^{4-}$-ion was remarkably broad in case of the samples subjected to the milling treatment for 5 minutes. However, the absorption peaks were changed to be sharp as the milling time was increased. This indicated that a crystallizing property of HAp was increased as the production amount of HAp was increased when the results such that the diffraction peak intensity at (211) surface of HAp was increased in the XRD measurement.

Next, a concrete embodiment in which a composite of HAp and an organic compound is manufactured by a wet-type milling will be explained as Example 2.

EXAMPLE 2

A silk fibroin (SF: mfd. by Idemitsu Sekiyu Kagaku K. K.) having an average grain size of 7 μm was selected as the organic compound. SF is a main component of natural silk yarn and classified to a hard fiber protein just like collagen. According to the knowledge of the inventors of this invention, SF was confirmed to have a high organism-affinity and confirmed to be a material having a relatively high durability against milling stress, so that there can be realized various composites when SF is treated in accordance with the method of this invention.

At first, a change in state of SF was investigated by mill-treating a diluted phosphoric acid solution in which the above SF was solely dispersed. Namely, ion-exchanged water was added to 13.3 $cm^3$ of phosphoric acid ($H_3PO_4$) solution (mfd. by Daisei Kagaku K. K.) having a percentage content of 85.0% thereby to prepare 200 $cm^3$ of diluted solution. Then, 13.5 g of the above SF fine particles were dispersed in the diluted solution thereby to prepare a slurry. Thereafter, the slurry was put into the casing 1 of the multi-ring medium type ultrafine mill (MICROS-O type: mfd. by K. K. Nara Kikai Seisakusho). Then, the milling treatment was conducted for 60 minutes under a condition that a rotation speed of the main shaft was set to 850 rpm.

Due to the above milling treatment, the average grain diameter of SF formerly being spherical particles having an average grain size of 7 μm was changed to be fine so as to have an average grain size of 0.5 μm. In addition, specific surface area of SF was increased and surface roughness of SF particles was also increased. Therefore, it was confirmed that a reaction activity of SF was increased.

Figure 5:
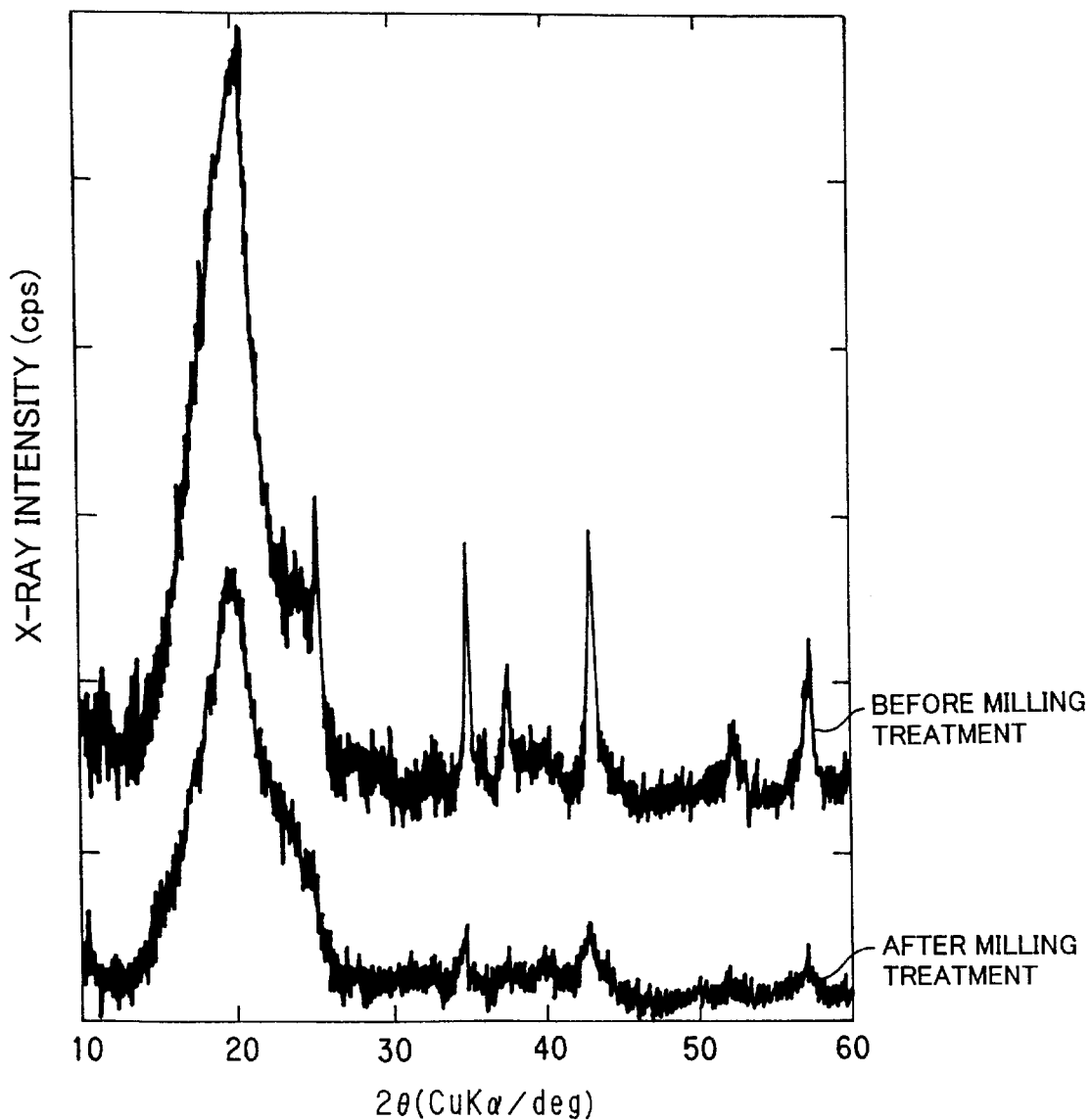
FIG. 5 is a graph showing an X-ray diffraction (XRD) profile of an SF particle.

With respect to the samples before and after the milling treatment was conducted, the powdery X-ray diffraction analysis was performed. The results are shown in FIG. 5. In case of the sample after the milling treatment, the intensity of each diffraction peaks was remarkably lowered in comparison with the sample after the milling treatment. In some cases, the diffraction peak was eliminated whereby the crystallizing property was lowered.

Figure 6:
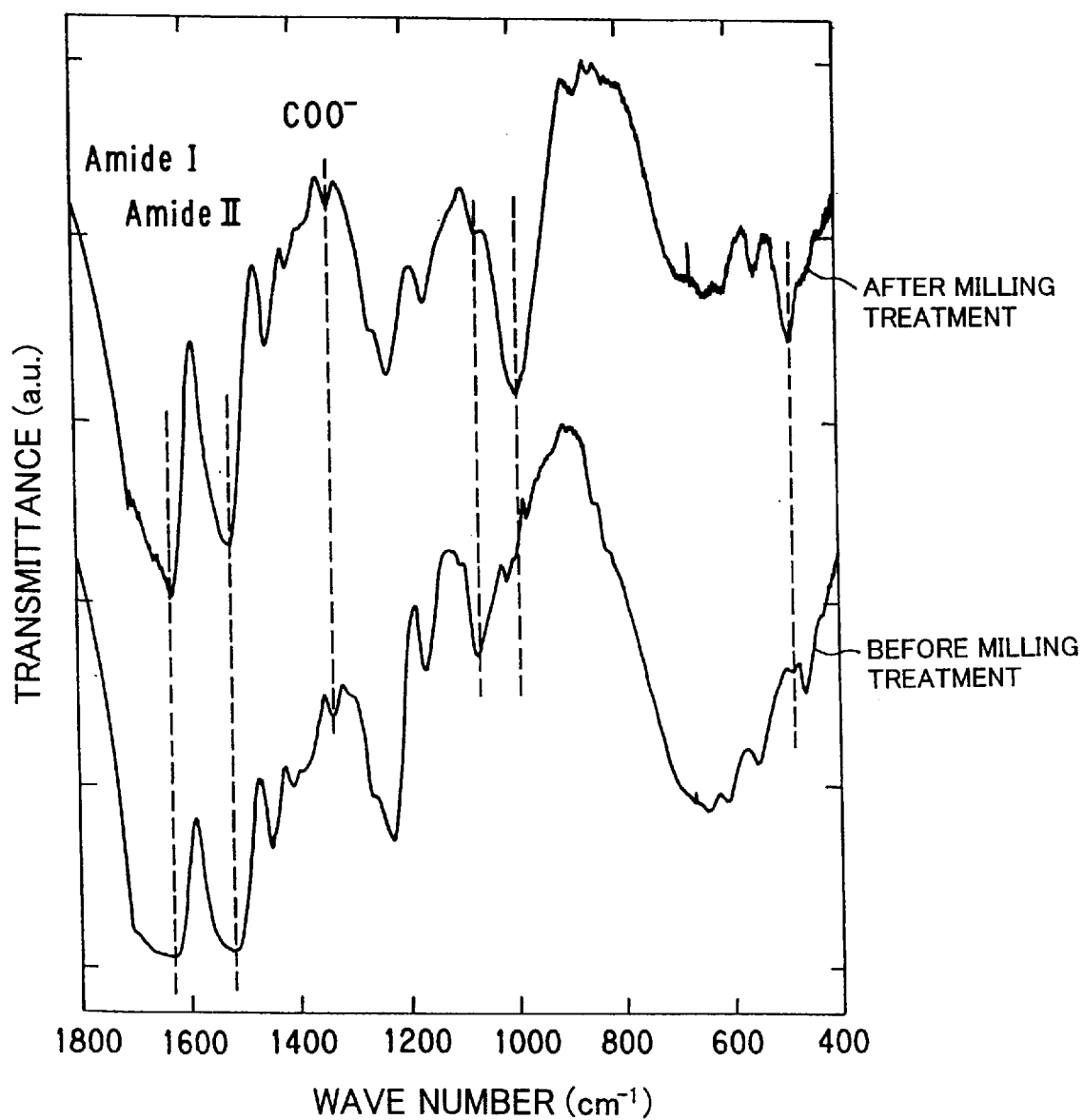
FIG. 6 is a graph showing an FT-IR spectrum of an SF particle.

With respect to the samples before and after the milling treatment was conducted, the infrared absorption (FT-IR) spectroscopic analysis was performed. The results are shown in FIG. 6. In case of the sample after the milling treatment, it was confirmed that an absorption peak of an amide bond (Amide I) mainly based on C=O stretching vibration at a wave number close to 1630 $cm^{-1}$ and an absorption peak of an amide bond (Amide II) mainly based on N-H deformation vibration at a wave number close to 1530 $cm^{-1}$ became sharp. In addition, there was no significant difference in position or intensity of the absorption peak based on —COO which was formed by ionizing terminal group (—COOH) of SF. Therefore, it was confirmed that there was hardly occur a breakage of the amide bonds of SF even after the milling treatment After the SF was subjected to the milling treatment in phosphoric acid solution, $Ca(OH)_2$ powder was added to the solution and then the milling treatment was again conducted whereby a HAp/SF composite was manufactured. Namely, 23.3 g of calcium hydroxide ($Ca(OH)_2$) powder (purity: 96.9%, mfd. by Wako Junyaku Kogyo K. K.) was weighed and put into the suspension obtained by conducting the pretreatment of SF in phosphoric acid solution so that the Ca/P molar ratio was controlled to be 1.67.

As the same manner as in Example 1, each of the suspensions was put into the casing 1 of the multi-ring medium type ultrafine mill (MICROS-O type: mfd. by K. K. Nara Kikai Seisakusho). Then, the mechanochemical milling treatment was conducted for 5 minutes, 15 minutes, 60 minutes and 180 minutes under a normal temperature and a condition that a rotation speed of the main shaft was set to 850 rpm. Then, with respect to each of thus milled suspensions, a suction filtration was conducted thereby to separate a product by the filtration. Subsequently, the product was dried for 24 hours in a temperature-controlled chamber in which the temperature was controlled to be 50° C. thereby to prepare HAp/SF composites of Example 2.

With respect to each of HAp/SF composites according to Example 2, an SEM observation was conducted. As a result, in case of the sample prepared by conducting the milling treatment for 5 minutes, it was confirmed that there existed needle-shaped crystals having a length of 200 nm and width of 30 nm. These crystals existed in a matrix of SF.

It was confirmed that the above needle-shaped crystals gradually decreased as the milling time was increased. In case of the sample prepared by conducting the milling treatment for 180 minutes, it was confirmed that an entire sample was changed into a spherical aggregated particle having a grain size of about 0.5 μm and having no anisotropy.

Figure 7:
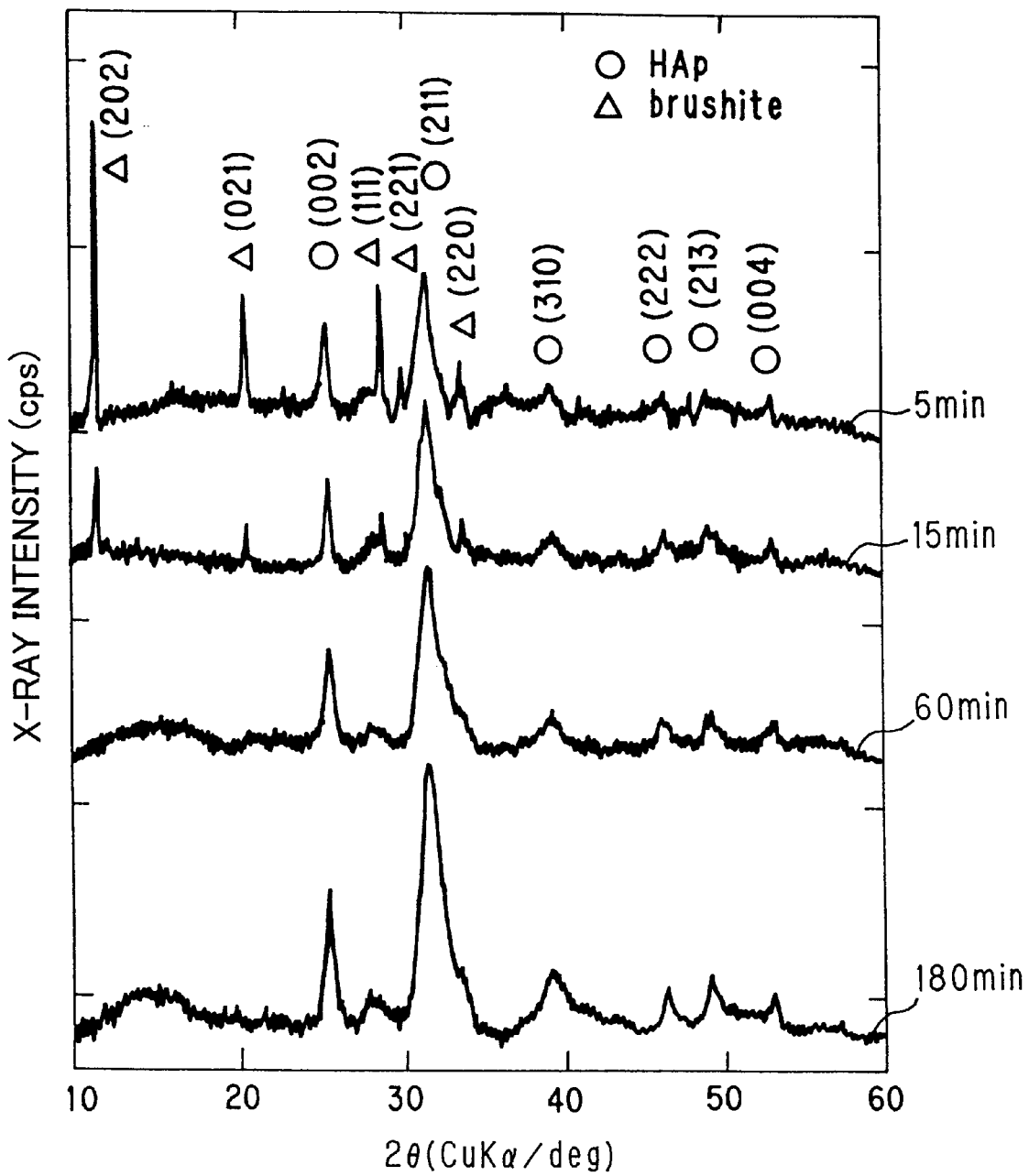
FIG. 7 is a graph showing an X-ray diffraction (XRD) profile of a HAp/SF composite in which a pretreatment of SF in a phosphoric acid solution is not conducted.
Figure 8:
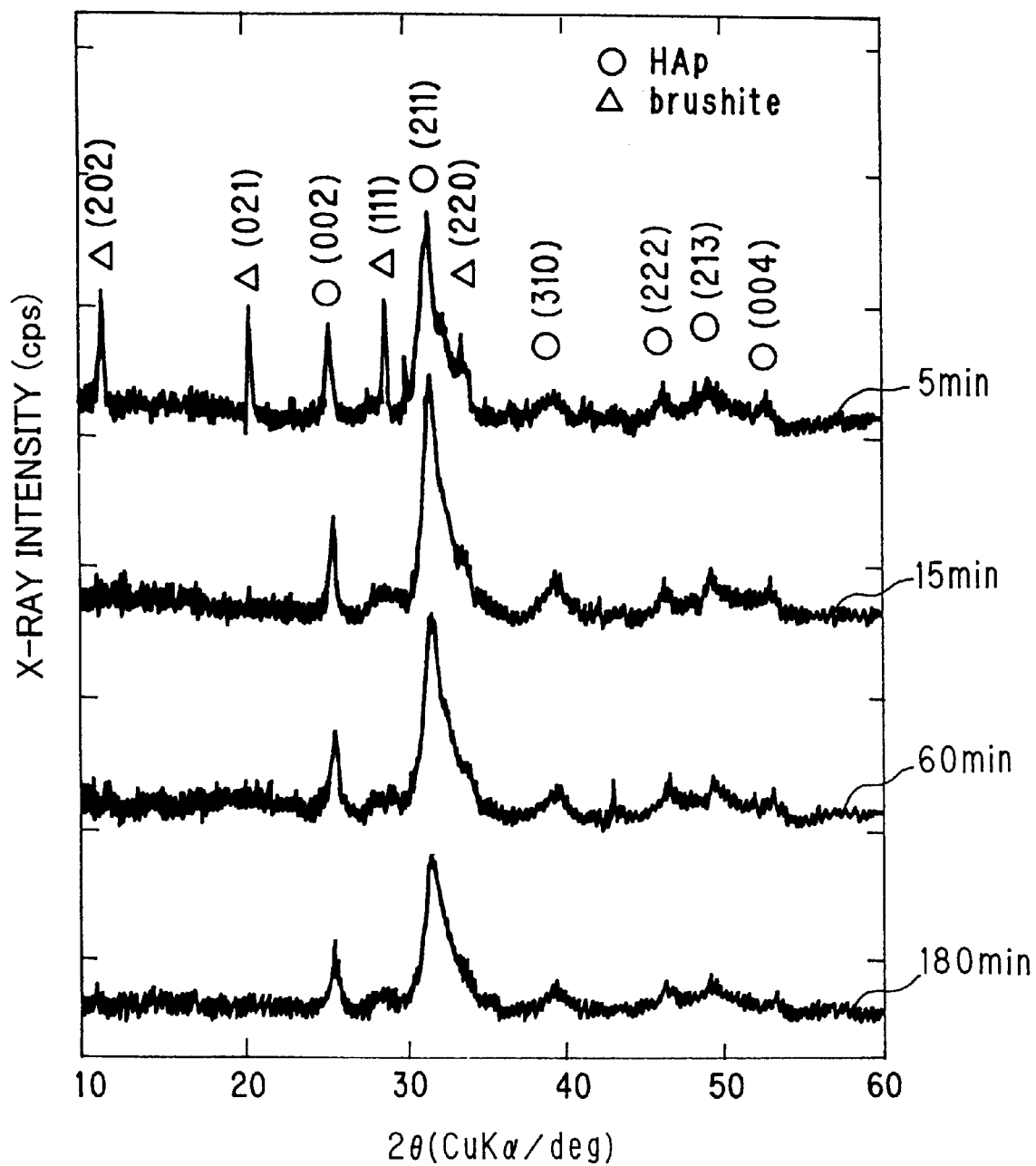
FIG. 8 is a graph showing an X-ray diffraction (XRD) profile of a HAp/SF composite in which a pretreatment of SF in a phosphoric acid solution is conducted.

In addition, with respect to each of the HAp/SF composite samples, the powdery X-ray diffraction analysis was performed. The results are shown in FIGS. 7 and 8 in which FIG. 7 is an XRD profile of HAp/SF composite prepared without conducting the pretreatment of SF being treated in the phosphoric acid solution, while FIG. 8 is an XRD profile of HAp/SF composite prepared by conducting the pretreatment.

In either case where the wet-type milling treatment for 5 minutes was conducted, HAp and BS as an intermediate product are coexisting. Further, the diffraction peak intensity of BS became higher in a case where SF prepared without conducting the pretreatment in the phosphoric acid solution was used. Therefore, it was confirmed that a degree of synthesizing reaction of HAp was lower in this case.

In addition, as the milling time increases, the diffraction peak of BS is changed to be eliminated and only the peak of HAp can be observed. This change is more quickly advanced in a case where SF with the pretreatment in the phosphoric acid solution is used. In a case where SF conducted the pretreatment is used as shown in FIG. 8, the diffraction peak of SF is eliminated by the pretreatment for 15 minutes. In contrast, in a case where SF without conducting the pretreatment is used as shown in FIG. 7, the diffraction peak of SF is eliminated by the pretreatment for 60 minutes. The reason of this difference is considered that a solubility of protein was increased by the pretreatment in the phosphoric acid solution whereby the dissolved protein had promoted the HAp forming reaction.

Figure 9:
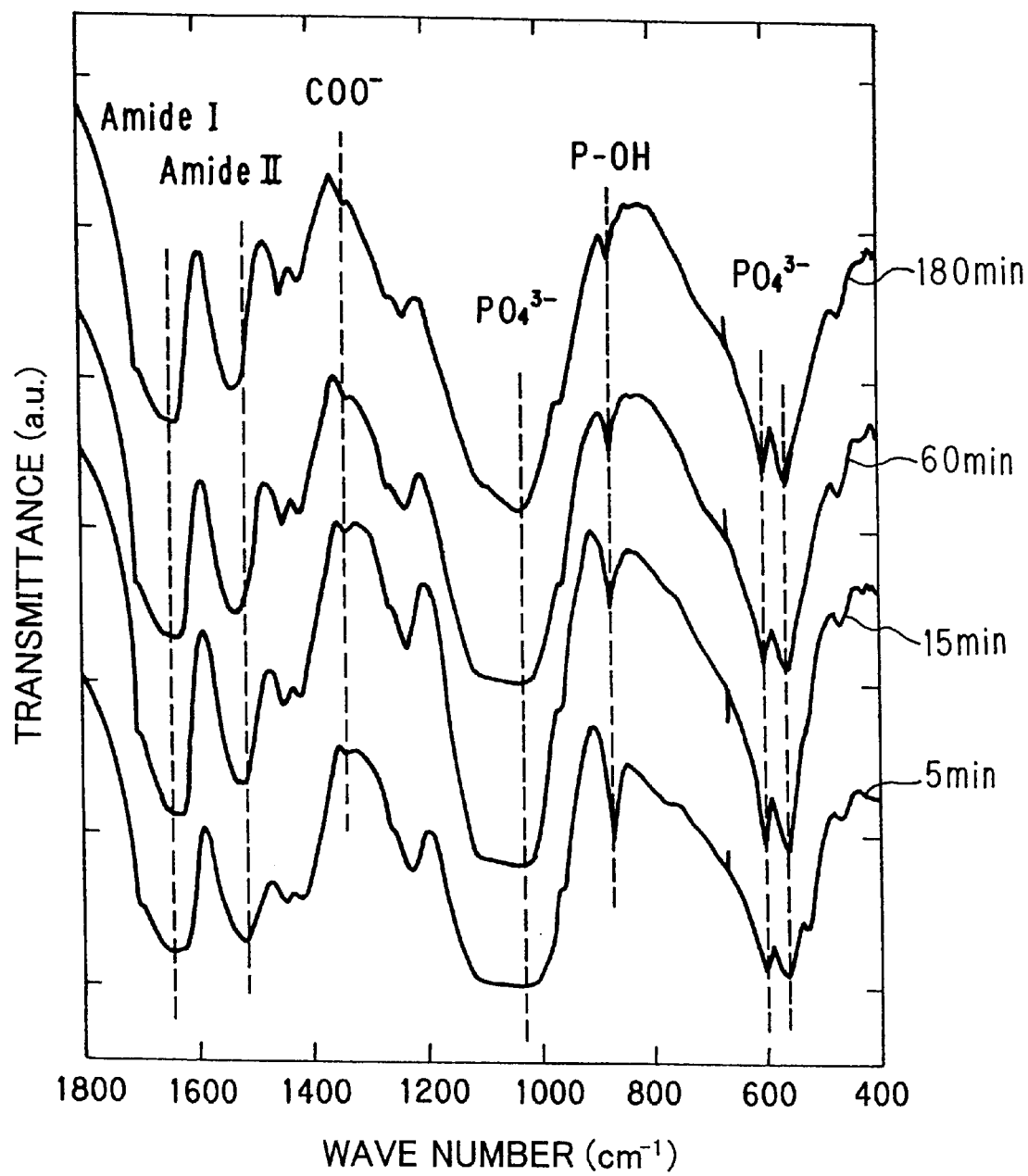
FIG. 9 is a graph showing a FT-IR spectrum of a HAp/SF composite in which a pretreatment of SF in a phosphoric acid solution is not conducted.
Figure 10:
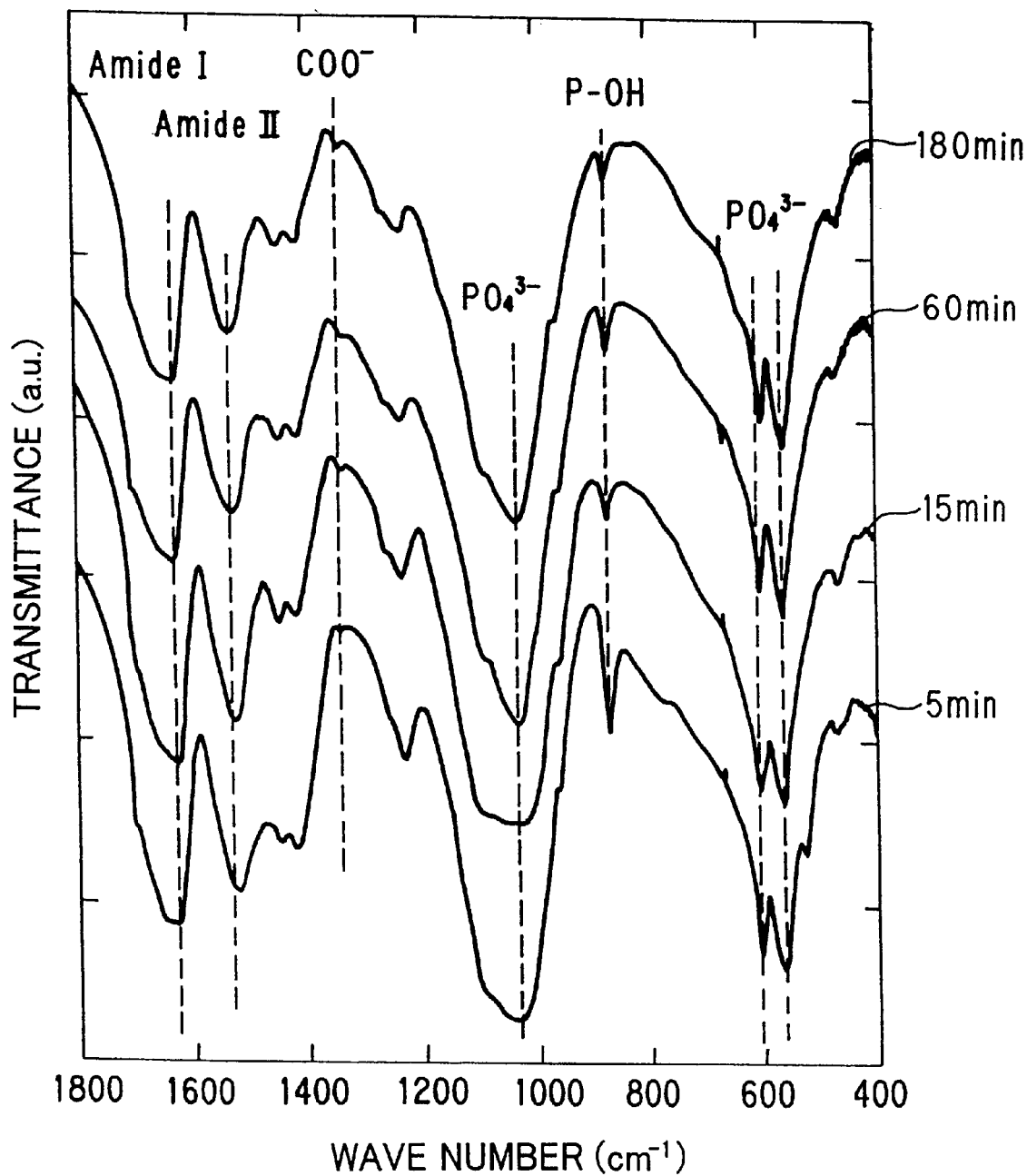
FIG. 10 is a graph showing a FT-IR spectrum of a HAp/SF composite in which a pretreatment of SF in a phosphoric acid solution is conducted.

In addition, with respect to each of the HAp/SF composite samples, the infrared absorption (FT-IR) spectrum analysis was performed. The results are shown in FIGS. 9 and 10 in which FIG. 9 is a FT-IR spectrum of HAp/SF composite prepared without conducting the pretreatment of SF being treated in the phosphoric acid solution, while FIG. 10 is a FT-IR spectrum of HAp/SF composite prepared by conducting the pretreatment.

In either case, the absorption peak intensity of P-OH stretching vibration at a wave number close to 875 cm$^{-1}$ was decreased as the milling time was increased and the absorption peak of $PO_4^{3-}$ ion became sharp. Such tendency is the same as XRD profile. In addition, even if the milling treatment is performed for 180 minutes, the absorption peak of P-OH is still remained and BS exists in an amorphous state. Further, it can be confirmed that there is formed Ca-defective type HAp in which $PO_4^{3-}$ ion site in the HAp structure is substituted by $HPO_4^{2-}$ ion. Furthermore, there can be observed a change in shape of the absorption peak of COO— ion originating from SE From this fact, the following knowledge is obtained. Namely, when SF is subjected to the pretreatment in the phosphoric acid solution, an interaction between SF and $Ca^{2+}$ ion occurs thereby to further promote the reaction of forming HAp.

Next, an embodiment of HAp/SF composite simultaneously synthesized by a conventional stirring treatment in place of the mechanochemical milling treatment will be explained with reference to the following Comparative Example 2.

COMPARATIVE EXAMPLE 2

HAp/SF composites of Comparative Example 2 were prepared by treating a the mixed material slurry before or after the pretreatment of SF was subjected to a stirring treatment for 12 hours by using a general purpose magnetic stirrer in place of the multi-ring medium type ultrafine mill used in Example 2.

When the above HAp/SF composites of Comparative Example 2 were observed by means of SEM, there were observed rod-shaped or blade-shaped BS crystals that had coarsely grown so that length of either crystal exceeded 10 µm, and the BS crystals were not fine grains like Example 2. Further, it was confirmed that there existed aggregated particles that are seemed to comprise SF or $Ca(OH)_2$. However, it was difficult to discriminate the two components.

Further, there was not observed a state of calcium phosphate being deposited as nucleus growing site on a surface of the SF particle. From this fact, it was confirmed that the synthesizing reaction of HAp was hardly advanced in spite of the stirring operation for a long time. By the way, regarding to influence of the pretreatment of SF particles in the phosphoric acid solution, there was no significant difference between the case with the pretreatment and the case without the pretreatment. In the both cases, the materials exhibited a non-uniformly mixed state.

Figure 11:
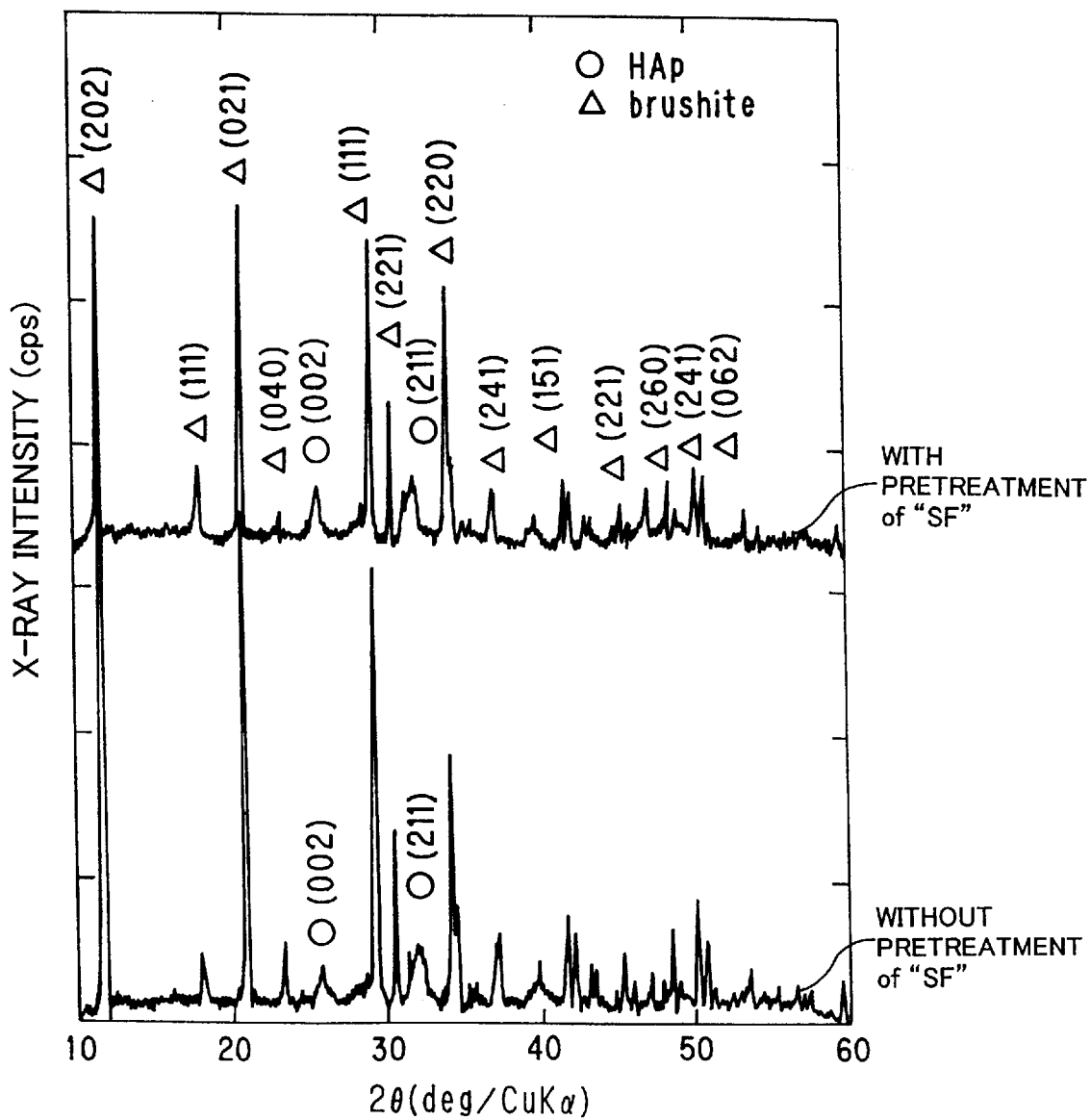
FIG. 11 is a graph showing an XRD profile of a HAp/SF composite of Comparative Example 2.

In addition, with respect to each of HAp/SF composites of Comparative Examples 2, the powdery X-ray diffraction (XRD) analysis was conducted. The results are shown in FIG. 11. In regardless of whether the pretreatment of SF in the phosphoric acid solution was conducted or not, the diffraction peaks of BS ($CaHPO_4.2H_2O$) as an intermediate product and HAp were observed in all cases. In addition, the diffraction peak intensity of BS was remarkably strong while small diffraction peaks of HAp at (002) surface and (211) surface were merely observed, so that a production amount of HAp was small.

Figure 12:
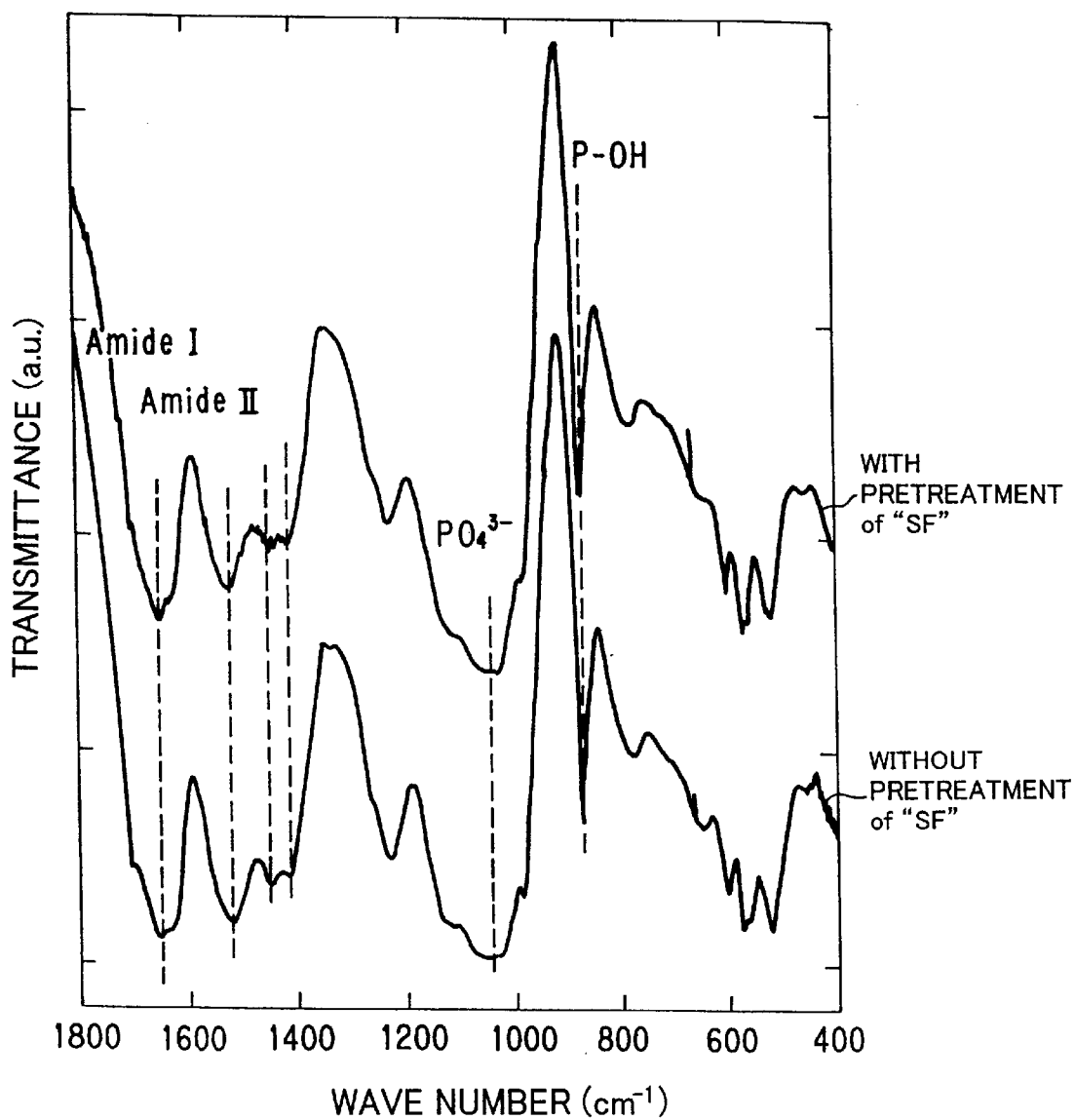
FIG. 12 is a graph showing a FT-IR spectrum of a HAp/SF composite of Comparative Example 2.
Figure 13:
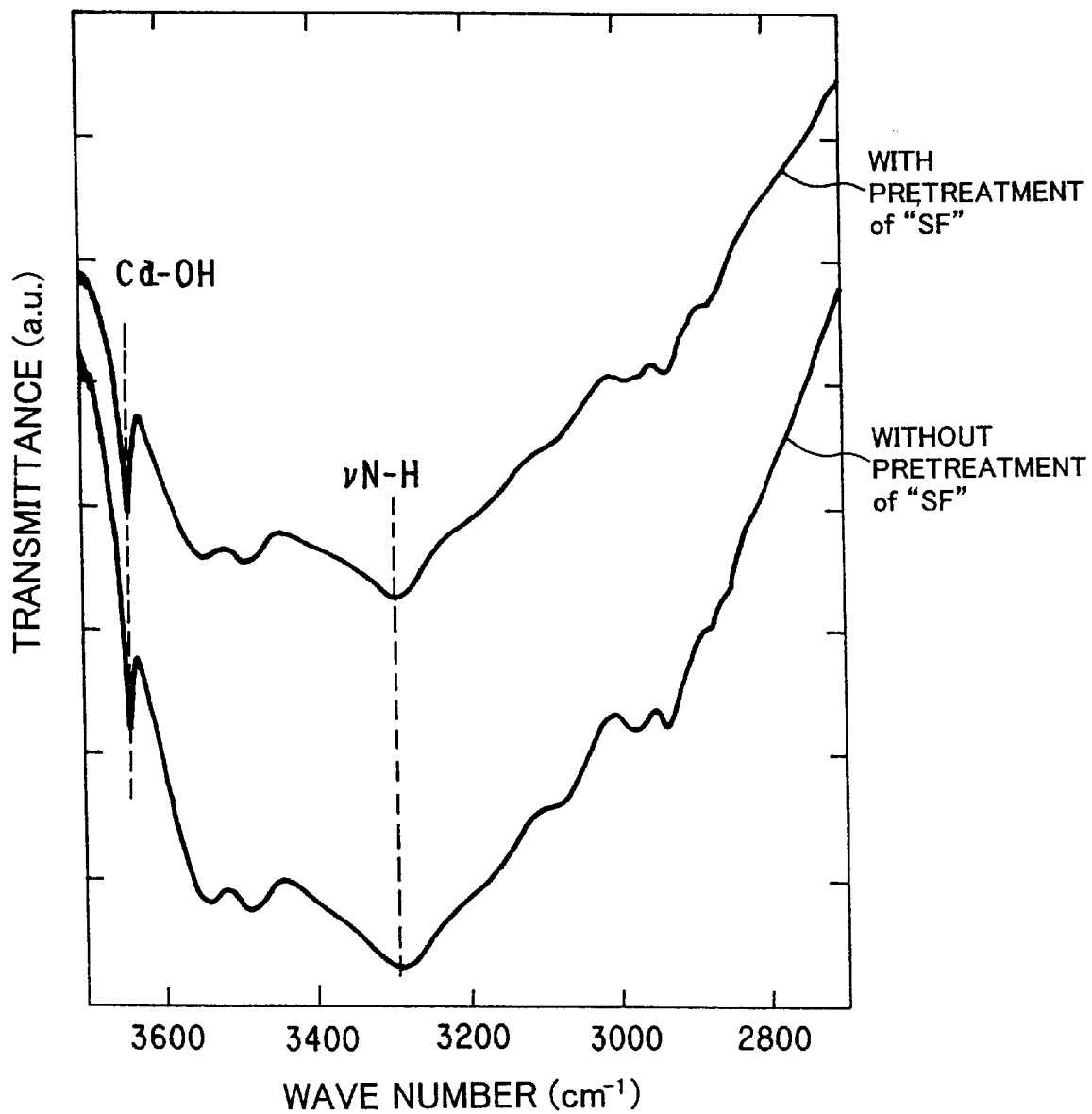
FIG. 13 is a graph showing a FT-IR spectrum of a HAp/SF composite of Comparative Example 2.

Furthermore, with respect to each of HAp/SF composites of Comparative Examples 2, the infrared absorption (FT-IR) analysis was conducted. The results are shown in FIGS. 12 and 13. As shown in FIG. 12, a diffraction peak of P-OH stretching vibration at a wave number close to 875 cm$^{-1}$ was observed, so that this evidenced the growth of BS as the same as in the above XRD measurement.

As shown in FIG. 13, at wave number of 3643 cm$^{-1}$ there is observed a peak due to hydroxyl group of $Ca(OH)_2$. In this regard, though the existence of $Ca(OH)_2$ was not confirmed in the XRD measurement, it was found that $Ca(OH)_2$ became amorphous during the stirring operation thereby to remain in the composite. From this fact, it was found that the reaction of forming BS by reacting $Ca(OH)_2$ with phosphoric acid ion in the liquid phase is moderately occurred.

As shown in the above comparative Example 2, the reaction of forming BS was advanced by the conventional stirring treatment, however, a converting reaction for converting into HAp was not occurred at all. Therefore, it was again confirmed that the conventional stirring treatment is not suitable as a method of manufacturing a uniform HAp/SF composite even if the treatment was conducted for a long time.

Next, a method of manufacturing a HAp/SF composite will be explained with reference to the following Comparative Example 3 which is formed by compositing HAp previously synthesized and SF.

COMPARATIVE EXAMPLE 3

$Ca(H_2PO_4)_2.H_2O$ (purity:90.0%, mfd.by Wako Junyaku Kogyo K. K.) and $Ca(OH)_2$ (purity:96.0%, mfd.by Wako Junyaku Kogyo K. K.) were mixed so as to prepare a mixture having a Ca/P ratio of 1.67. Then, 50 g of thus obtained mixture was put into the ultrafine mill shown in FIGS. 1 and 2. Thereafter, a milling treatment of dry-method was conducted in atmosphere under the rotating speed of 1250 rpm for 180 minutes thereby to synthesize HAp.

Thus obtained HAp and SF used in Example 2 were mixed so as to have a weight ratio (HAp/SF) of 9/1 thereby to obtain a mixture. Then, 50 g of thus obtained mixture was put into the ultrafine mill (MICROS-O type) shown in FIGS. 1 and 2. Thereafter, a milling treatment of dry-method was conducted for each of the mixtures as the same manner as in Example 2 except that the rotation speed was set to 850 rpm and the milling treatment was performed for 0 minute, 30 minutes and 180 minutes, thereby to manufacture HAp/SF composites of Comparative Example 3 respectively through the dry-process.

When HAp/SF mixture obtained by the treatment for 180 minutes was observed by means of TEM, it was confirmed that SF particles had been pulverized to be fine particles having grain size of about 0.1 μm and the SF fine particles are existing around of HAp particles having grain size of about 2 μm.

Figure 14:
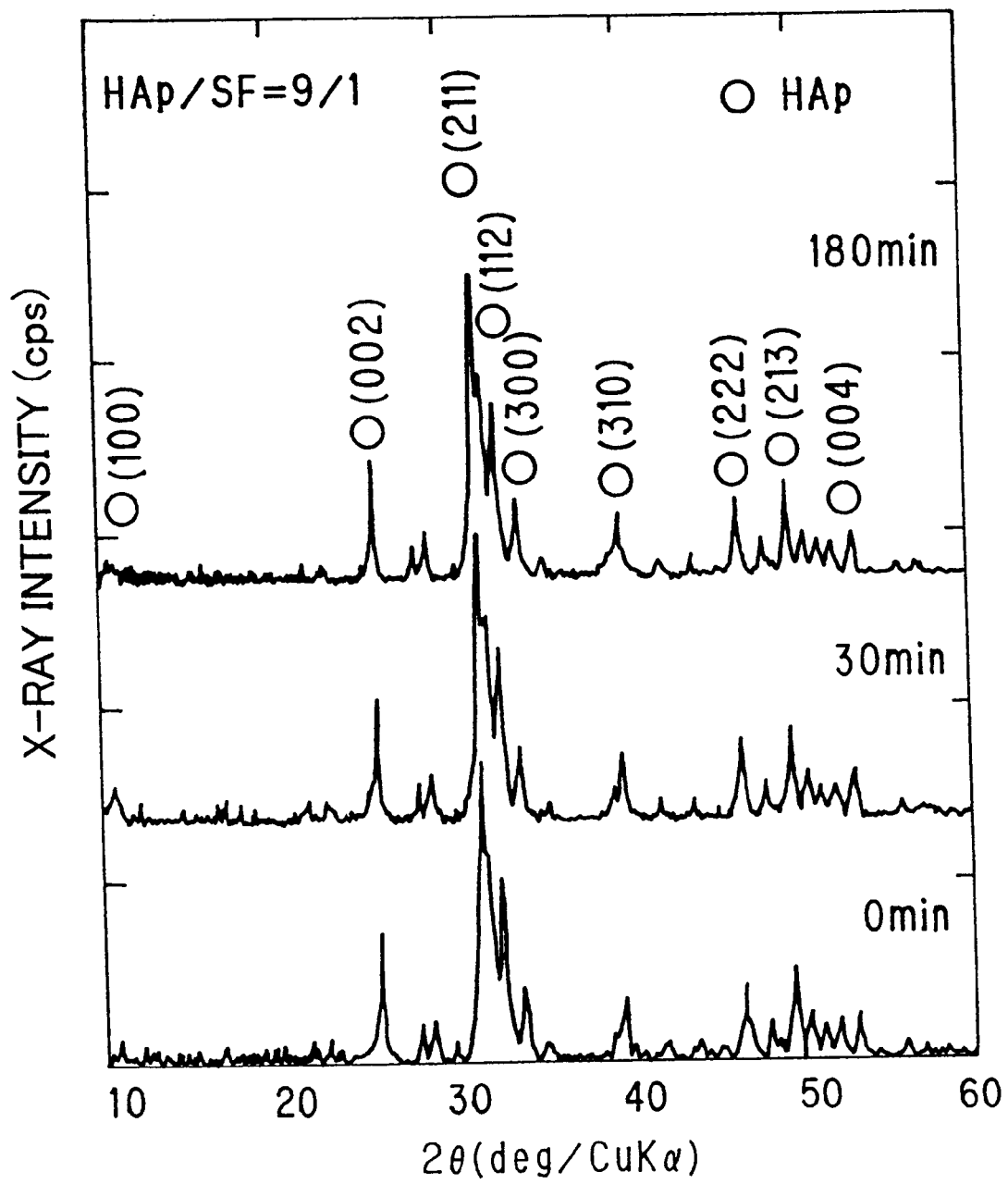
FIG. 14 is a graph showing an XRD profile of a HAp/SF composite of Comparative Example 3.

Further, a change in crystallizing state of the composite during the milling treatment was observed by means of X-ray diffraction (XRD). The results shown in FIG. 14 was obtained. That is, as the milling time was increased, a diffraction peak originated from apatite was shifted to a high angle side. As indicated by the changing formula: $H_2PO_4^- \rightarrow HPO_4^{2-} \rightarrow PO4^{3-}$, the above shift is considered to occur by shrinkage of Ap-lattice, the shrinkage being caused by the advance of detachment of remaining hydrogen. Note, FT-IR spectrum derived from SF was not changed even the milling time was increased, so that a chemical interaction between HAp and SF did not occur.

As described above, according to the method of Comparative Example 3 in which HAp/SF composite is manufactured by the milling treatment of HAp and SF in dry-process, there is no significant change in the state between HAp and SF, but there is obtained a simple mixed state of the both components. In contrast to this, in the method of Example 2 in which the synthesize of HAp and the compositing the SF are simultaneously advanced, a change in the FT-IR spectrum of SF is great due to the milling treatment, and hydrogen bonding state between SF and another SF or between SF and HAp is greatly changed. In addition, in a case where $Ca(OH)_2$, $H_3PO_4$ and SF are subjected to the milling treatment in wet-process, there is recognized a sign of that the reaction between phosphoric acid ion and SF is taken place with high priority. Therefore, it can be said that the method of Example 2 in which the mechanochemical milling treatment is performed in dry-process is more effective.

In the respective embodiments of the present invention, when the above dehydrated and dried HAp or the composite thereof is compressed by a uniaxial compression method, a biaxial compression method, or a cold isostatic pressing (CIP) method, there can be formed a densified organism bone alternating material having an arbitrary-shape.

Furthermore, since the HAp slurry (HAp composite slurry) obtained by being subjected to the mechanochemical milling treatment can be provided as fine crystal slurry with a good dispersibility, when this slurry is molded by a casting method, there can be formed a densified organism material having an arbitrary-shape. In addition, when the above slurry is coated onto various substrates, it is extremely easy to form a thin film.

For example, when a substrate composed of metal or ceramics, or an organic substrate composed of organic substances such as nylon, cuttlefish skin, chitosan or the like having a flexibility is dipped into the above slurry, thereafter, the dipped substrate is pulled up from the slurry, then the slurry is dried at a room temperature, so that there can be obtained an organism material in which a dense HAp layer or film or HAp composite film is integrally formed onto the surface of the substrate. In particular, in a case where the substrate material has a hydrophilic functional group such as hydroxyl group, the affinity with the HAp slurry is improved to be high, and there can be formed a film having a high density and uniformity and capable of suppressing the crack formation.

INDUSTRIAL APPLICABILITY

As explained above, according to the method of synthesizing hydroxy apatite, hydroxy apatite composite and the method of manufacturing the composite of the present invention, the HAp powder is formed by conducting the mechanochemical milling treatment imparting shearing force and compressive force based on the centrifugal force of the mechanically rotating body, so that a fine crystal HAp powder having a uniform size or the composite thereof can be manufactured in a short time through a simple process even under the conditions of normal temperature and pressure.

Further, when the organic compound particles are contained in the mixed material slurry and HAp is synthesized under a condition of existing the organic compound, the HAp composite comprising HAp and the organic compound can be easily manufactured through a single process under the normal temperature and pressure.

In particular, the particle size of each of the HAp powder and the composite thereof is fine to be about 50 nm and a dispersing state of the particles is also excellent, so that a dense organism material having less crackformation can be formed whereby it is possible to provide the organism material having high durability and reliability.

What is claimed is:

1. A hydroxy apatite composite comprising hydroxy apatite particles formed by reacting calcium hydroxide ($Ca(OH)_2$) with phosphoric acid ($H_3PO_4$) under a condition of existing organic compound particles and the organic compound particles of which surfaces are integrally formed and composited with said hydroxy apatite particles
   wherein said hydroxy apatite is manufactured by a synthesizing method comprising the steps of:
      preparing a mixed material slurry by dispersing calcium hydroxide ($Ca(OH)_2$) powder into a phosphoric acid ($H_3PO_4$) solution;
      conducting a mechanochemical milling treatment in which shearing force and compressive force based on a centrifugal force of a mechanical rotating body are imparted to the mixed material slurry, wherein a centrifugal effect imparted to the slurry by the centrifugal force of the mechanochemical milling treatment is 15 or more; and
      reacting the calcium hydroxide component with the phosphoric acid component under normal temperature and pressure thereby to prepare hydroxy apatite (HAp) powder having fine crystals.

2. The hydroxy apatite composite according to claim 1, wherein a Ca/P molar ratio in said mixed material slurry is set to a range of 1.2–1.8.

3. The hydroxy apatite composite according to claim 1, wherein $CO_3^{2-}$ group is introduced into said hydroxy apatite (HAp) by substituting a part of calcium hydroxide ($Ca(OH)_2$) with calcium carbonate ($CaCO_3$).

4. The hydroxy apatite composite according to claim 1, wherein a solid content of said mixed material slurry is set to a range of 5–40 wt %.

5. The hydroxy apatite composite according to claim 1, wherein said organic compound comprises fiber protein which comprises at least one of silk fibroin (SF) and collagen.

6. The hydroxy apatite composite according to claim 5, wherein a ratio of said fiber protein to said composite is set to 10–90 wt %.

7. The hydroxy apatite composite according to claim 1, further comprising an organic substrate having flexibility and hydroxy apatite (HAp) film integrally formed on said organic substrate.

8. The hydroxy apatite composite according to claim 7, wherein said organic substrate having flexibility comprises at least one of nylon, cuttlefish skin and chitosan.

9. A method of manufacturing a hydroxy apatite composite comprising the steps of:
preparing a mixed material slurry by dispersing calcium hydroxide (Ca(OH)$_2$) powder into a phosphoric acid (H$_3$PO$_4$) solution,
conducting a mechanochemical milling treatment in which shearing force and compressive force based on a centrifugal force of a mechanical rotating body are imparted to said mixed material slurry,
wherein a centrifugal effect imparted to said mixed material slurry by the centrifugal force of the mechanochemical milling treatment is 15 or more,
adhering the obtained mixed material slurry to a surface of an organic substrate, and
drying said mixed material slurry whereby a hydroxy apatite (HAp) film is integrally formed to the surfaces of said organic substrate.

10. A method of manufacturing a hydroxy apatite composite comprising the steps of:
preparing a mixed material slurry by dispersing calcium hydroxide (Ca(OH)$_2$) powder and organic compound particles into a phosphoric acid (H$_3$PO$_4$) solution,
conducting a mechanochemical milling treatment in which shearing force and compressive force based on a centrifugal force of a mechanical rotating body are imparted to said mixed material slurry,
wherein a centrifugal effect imparted to the slurry by the centrifugal force of the mechanochemical milling treatment is 15 or more; and
reacting the calcium hydroxide component with the phosphoric acid component under normal temperature and pressure thereby to prepare hydroxy apatite (HAp) powder having fine crystals,
whereby said hydroxy apatite (HAp) powder having fine crystals is deposited onto surfaces of said organic compound particles, and whereby simultaneously said hydroxy apatite powder and said organic compound particles are composited.

11. The method according to claim 10, wherein said organic compound particles are subjected to the mechanochemical milling treatment in advance in a phosphoric acid solution so that said phosphoric acid ion having affinity is adhered to the surface of the organic compound particles.

12. The method according to claim 10, wherein a Ca/P molar ratio of said mixed material slurry is set to a range of 1.2–1.8.

13. The method according to claim 10, wherein a solid content of said mixed material slurry is set to a range of 5–40 wt %.

14. The method according to claim 10, wherein said organic compound is formed of fiber protein composed of at least one of silk fibroin (SF) and collagen.

15. The method according to claim 10, wherein a ratio of said fiber protein to the composite is set to 10–90 wt %.

16. The method according to claim 10, wherein said mechanochemical milling treatment for the mixed material slurry is performed by means of a multi-ring type ultrafine mill comprising a number of ring-shaped pulverizing media.

17. The hydroxy apatite composite according to claim 1, wherein said hydroxy apatite particle is a nano-sized grain.

18. The hydroxy apatite composite according to claim 1, wherein said hydroxy apatite particle has an average grain size of 50 nm or less.

19. The hydroxy apatite composite according to claim 1, wherein said organic compound particles are subjected to the mechanochemical milling treatment in advance in a phosphoric acid solution so that said phosphoric acid ion having affinity is adhered to the surface of the organic compound particles.

20. The hydroxy apatite composite according to claim 1, wherein said mechanochemical milling treatment for the mixed material slurry is performed by means of a multi-ring type ultrafine mill comprising a number of ring-shaped pulverizing media.

21. The hydroxy apatite composite according to claim 5, wherein a ratio of said fiber protein to said composite is set to 10–40 wt. %.

22. The hydroxy apatite composite according to claim 1, wherein a solid content of said mixed material slurry is set to a range of 10–35 wt. %.

23. The hydroxy apatite composite according to claim 1, wherein said centrifugal effect is 70 or more.

24. The hydroxy apatite composite according to claim 1, further comprising a substrate selected from the group consisting of metals, ceramics and polymers with said composite thereon.

* * * * *